United States Patent
Gross et al.

(10) Patent No.: US 8,864,848 B2
(45) Date of Patent: Oct. 21, 2014

(54) ZWITTERIONIC AZO DYESTUFFS FOR COLORING KERATIN-INCLUDING FIBRES

(71) Applicant: Henkel AG & Co. KGaA, Düsseldorf (DE)

(72) Inventors: Wibke Gross, Hückelhoven (DE); Ralph Nemitz, Jüchen (DE); Melanie Moch, Dormagen (DE)

(73) Assignee: Henkel AG & Co. KGAA, Duesseldorf (DE)

(*) Notice: Subject to any disclaimer, the term of this patent is extended or adjusted under 35 U.S.C. 154(b) by 0 days.

(21) Appl. No.: 14/270,175

(22) Filed: May 5, 2014

(65) Prior Publication Data

US 2014/0237735 A1    Aug. 28, 2014

Related U.S. Application Data

(63) Continuation of application No. PCT/EP2012/070741, filed on Oct. 19, 2012.

(30) Foreign Application Priority Data

Nov. 8, 2011   (DE) .......................... 10 2011 085 906

(51) Int. Cl.
| | |
|---|---|
| *A61Q 5/10* | (2006.01) |
| *C07D 277/42* | (2006.01) |
| *C07D 211/00* | (2006.01) |
| *C07D 261/14* | (2006.01) |
| *A61K 8/49* | (2006.01) |
| *C07D 285/135* | (2006.01) |
| *C07D 235/30* | (2006.01) |
| *C07D 263/58* | (2006.01) |
| *C07D 233/88* | (2006.01) |
| *C07D 213/76* | (2006.01) |
| *C07D 249/14* | (2006.01) |
| *C07D 277/82* | (2006.01) |
| *C07D 231/38* | (2006.01) |
| *C07D 285/08* | (2006.01) |

(52) U.S. Cl.
CPC ............ *A61K 8/4946* (2013.01); *C07D 261/14* (2013.01); *A61K 8/49* (2013.01); *C07D 285/135* (2013.01); *C07D 235/30* (2013.01); *C07D 263/58* (2013.01); *C07D 233/88* (2013.01); *C07D 213/76* (2013.01); *C07D 277/42* (2013.01); *C07D 249/14* (2013.01); *C07D 277/82* (2013.01); *A61K 8/4926* (2013.01); *A61Q 5/10* (2013.01); *C07D 231/38* (2013.01); *C07D 285/08* (2013.01)
USPC ................ 8/405; 8/409; 8/568; 8/570; 8/573; 548/146; 548/215; 548/300.1; 548/355.1; 546/249

(58) Field of Classification Search
CPC ......... A61Q 5/10; A61K 8/49; A61K 8/4926; A61K 8/4946; C07D 249/14; C07D 277/42; C07D 231/38; C07D 263/58; C07D 261/114; C07D 285/08; C07D 285/135
USPC .............. 8/405, 409, 568, 570, 573; 548/146, 548/215, 300.1, 355.1; 546/249
See application file for complete search history.

(56) References Cited

FOREIGN PATENT DOCUMENTS

| | | | |
|---|---|---|---|
| EP | 1915984 A1 * | 10/2006 | ............... A61Q 5/10 |
| EP | 1915984 A1 | 4/2008 | |
| WO | 2006081245 A1 | 8/2006 | |

OTHER PUBLICATIONS

Stic Search Rewport dated May 27, 2014.*

* cited by examiner

*Primary Examiner* — Eisa Elhilo
(74) *Attorney, Agent, or Firm* — Steven L. Nichols; Van Cott, Bagley, Cornwall & McCarthy P.C.

(57) ABSTRACT

The invention relates to agents for coloring keratinic fibers, in particular human hair, including in a cosmetic carrier at least one compound of the formula (I). The structures the of the general formula (I) have a heterocycle A which bears a quaternary nitrogen atom and thus a positive charge. The invention furthermore relates to the use of these novel azo dyes in agents for coloring hair and to the dyes themselves.

15 Claims, No Drawings

ZWITTERIONIC AZO DYESTUFFS FOR COLORING KERATIN-INCLUDING FIBRES

RELATED DOCUMENTS

The present application claims benefit and is a continuation of International Application No. PCT/EP2012/070741, filed Oct. 19, 2012, which claims the benefit of the filing date of German Patent Application No. 10 2011 085 906.3 filed Nov. 8, 2011. These applications are incorporated herein by reference in their entireties.

DETAILED DESCRIPTION

The present invention relates to agents for coloring keratinic fibers, in particular human hair. The agents include novel zwitterionic azo dyes. The invention furthermore relates to the use of these novel azo dyes in agents for coloring hair and to the dyes themselves.

In general, it is either substantive dyes or oxidation dyes which are used for dyeing keratinic fibers. Although intense colorings with good fastness properties may be achieved with oxidation dyes, the color is generally developed under the influence of oxidizing agents such as, for example, $H_2O_2$, which may in some cases result in damage to the fibers. Moreover, some oxidation dye precursors or certain mixtures of oxidation dye precursors may have a sensitizing effect in people with sensitive skin. Substantive dyes are applied under milder conditions. The disadvantage thereof, however, is that the colorings frequently exhibit only inadequate fastness characteristics. This is particularly the case when the hair is washed, but also occurs in relation to external influences, such as sunlight or reactive environmental chemicals, such as, for example, swimming pool water. Substantive dyes are frequently also used for shading oxidative colorings. One particular challenge for hair coloring using substantive dyes is uniformly coloring frequently pretreated hair, such as, for example, bleached or permed hair, in which the fibers have highly variable levels of prior damage at different lengths or in differently treated areas. During the actual coloring, the coloring agent may exhibit uneven coloring behavior on hair suffering differing levels of prior damage. However, repeated hair washing may also wash out the dyes to varying extents in the different areas of hair, leading to a non-uniform and, thus, unwanted coloring result.

Strong lightening of dark hair involves using not only hydrogen peroxide alone, but also a combination of hydrogen peroxide and persulfates such as, for example, ammonium persulfate, potassium persulfate and/or sodium persulfate. Accordingly, if it is desired in one step to strongly lighten dark hair and simultaneously color it in a bright color shade, it is advantageous to use a mixture of hydrogen peroxide, persulfates and a substantive dye. Although a person skilled in the art will be aware of many substantive dyes with an intense coloring action for coloring hair, he or she will only be aware of a very limited selection of dyes which may withstand the strong oxidative conditions, as provided by a mixture of the above-stated oxidizing agents, without breaking down. In addition, the dyes with oxidation stability known from the prior art exhibit serious disadvantages with regard to other fastness characteristics.

There is accordingly still a requirement for dyes for simultaneously coloring and strongly lightening hair which have elevated stability towards strong oxidizing agents. Even under these extreme conditions of use, these dyes should not lose their positive fastness and coloring characteristics.

The object of the present application is therefore to provide coloring agents for keratinic fibers, in particular human hair, which exhibit good applicational properties with regard to color depth and fastness characteristics, such as in particular light, abrasion and washing fastness as well as sweat and cold perming fastness. Finally, it is particularly desirable to provide coloring agents with a good equalizing capacity. In the case of simultaneous use with oxidation dyes and/or oxidizing agents, the substantive dyes should have sufficient stability towards hydrogen peroxide and other oxidizing agents and not lose their positive fastness and coloring characteristics. In addition, it should be possible to achieve the brightest and most intense colorings possible.

It has been found that bright and intense colorings may in particular be produced with cationic substantive dyes. Cationic dyes are often distinguished by particularly elevated affinity for keratin fibers, a characteristic which may be attributed to the interactions of the positive charges of the dyes with negatively charged structural components of the keratinic fibers. Accordingly, it is often possible to achieve particularly intense colorings with cationic dyes. However, due to the positive charge present in their molecular structure, many of these dyes are also susceptible to hydrolytic cleavage, which has a disadvantageous impact on the storage stability of the compounds. When stored in formulated form, many cationic dyes, therefore, have only inadequate storage stability. This lack of stability is particularly pronounced if the formulations are alkaline. A further object of the present invention is, accordingly, to provide novel, intensely coloring dyes with elevated affinity for keratin fibers which, even on extended storage in formulated form, do not undergo degradation processes and, in particular, have an elevated stability towards alkalizing agents and alkaline formulations.

It has surprisingly been found that specific zwitterionic azo dyes, which have both a positive charge within the chromophore and a sulfuric acid ester grouping connected to the chromophore via a linker unit, are highly suitable as substantive dyes for hair coloring. When used for coloring, intense color shades with very good fastness characteristics are obtained. This is particularly the case in the presence of oxidizing agents. When the dyes are incorporated into cosmetic, alkaline formulations they exhibit good storage stability. When oxidizing agents such as hydrogen peroxide or a mixture of hydrogen peroxide and persulfate are simultaneously used, these substantive dyes likewise provide intense shades without any attenuation of color intensity and color brightness. In this manner, it is possible to simultaneously brighten and color hair. Consequently, it is also possible to achieve a bright color result even on dark hair.

EP 1915984 discloses azo dyes including a cationic, specifically substituted thiazole unit as hair coloring agents. The dye molecules stated therein include a phenyl-azo unit which may comprise a sulfuric acid ester grouping bridged via an alkyl group. Coloring agents including zwitterionic azo dyes according to formula (I), below, have not previously been known as hair dyes.

The present invention firstly provides an agent for coloring keratinic fibers, in particular human hair, including in a cosmetic carrier at least one compound of the formula (I),

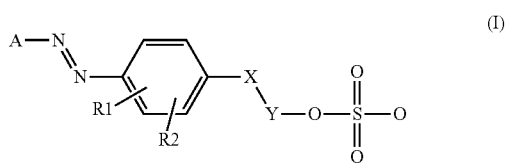

in which R1 and R2 mutually independently denote hydrogen, a $C_1$-$C_6$ alkyl group, a $C_2$-$C_6$ alkenyl group, a hydroxyl group, a $C_1$-$C_6$ alkoxy group, halogen, an amino group, an acetylamino group, a nitro group or a nitrile group. Alternatively, R1 and R2 form a 5- or 6-membered, saturated or unsaturated, carbocyclic or heterocyclic ring, provided they are in ortho position relative to one another. X denotes O or N—R3, and R3 denotes hydrogen, a $C_1$-$C_6$ alkyl group, a $C_2$-$C_6$ alkenyl group, a $C_2$-$C_6$ hydroxyalkyl group, a $C_2$-$C_6$ polyhydroxyalkyl group, a $C_1$-$C_6$ cyanoalkyl group, an aryl-$C_1$-$C_6$-alkyl group or a group —Y'—O—SO$_2$—OM. Y and Y', in each case, mutually independently denote $(CH_2)_n$ or $C_2H_4$—$(OC_2H_4)_n$ or $(CH_2)_n$—O—$(CH_2)_m$ or $(CH_2)_n$—N(R8)-$(CH_2)_m$ and n and optionally m in each case mutually independently denote an integer from 1 to 6. A denotes one of structures (II) through (XIII) below,

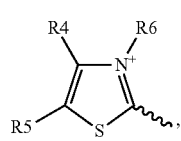 (II)

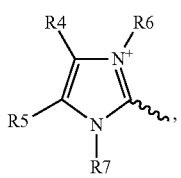 (III)

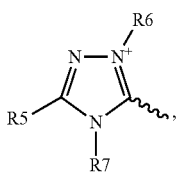 (IV)

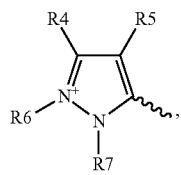 (V)

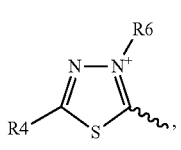 (VI)

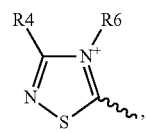 (VII)

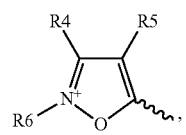 (VIII)

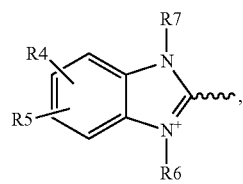 (IX)

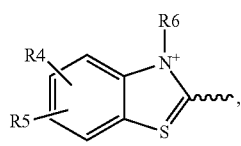 (X)

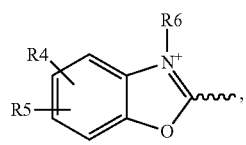 (XI)

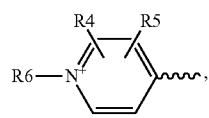 (XII)

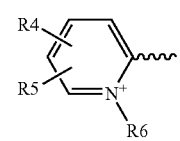 (XIII)

in which R4 and R5, in each case, mutually independently denote hydrogen, a $C_1$-$C_6$ alkyl group, a $C_2$-$C_6$ alkenyl group, a hydroxyl group, a $C_1$-$C_6$ alkoxy group, halogen, an amino group, an acetylamino group, a $C_1$-$C_6$ alkylsulfonyl group or a nitrile group Alternatively, R4 and R5 form a 5- or 6-membered, saturated or unsaturated, carbocyclic or heterocyclic ring, provided they are in ortho position relative to one another. R6 and R7 mutually independently denote a $C_1$-$C_6$ alkyl group, a $C_2$-$C_6$ alkenyl group or a $C_2$-$C_6$ hydroxyalkyl group. R8 denotes hydrogen, a $C_1$-$C_6$ alkyl group, a $C_2$-$C_6$ alkenyl group or a $C_2$-$C_6$ hydroxyalkyl group, and M denotes hydrogen, an alkali metal or half an equivalent of an alkaline earth metal.

Keratinic fibers, keratin—including fibers or keratin fibers should here be taken to mean furs, wool, feathers and, in particular, human hair. Although the agents according to the invention are primarily suitable for lightening keratin fibers, there is no reason in principle why they should not also be used in other fields.

The phrase "coloring of keratin fibers" used according to the invention includes any kind of color modification of the fibers, and, in particular, the color modifications known by the terms tinting, blonding, lightening, bleaching, oxidative coloring, semipermanent coloring, permanent coloring and temporary coloring. Color modifications which provide a lighter coloring result than the initial color, such as for example blonding with coloring, are explicitly also included according to the invention.

The agents according to the invention include the compounds of the formula (I) in a cosmetic carrier. This cosmetic carrier is preferably aqueous, alcoholic, or aqueous-alcoholic. Carriers suitable for the purpose of hair treatment are for example creams, emulsions, gels or also surfactant—including foaming solutions, such as, for example, shampoos, foam aerosols or other preparations which are suitable for use on the hair. It is, however, also possible to provide a formulation in powder or tablet form for storage. Said formulation is then mixed before use in an aqueous solvent or with organic solvents or with mixtures of water and organic solvents to obtain the mixture for use. An aqueous carrier includes, for the purposes of the invention, at least 40 wt. %, in particular at least 50 wt. %, water. For the purposes of the present invention, aqueous-alcoholic solutions should be taken to be aqueous solutions including 3 to 70 wt. % of a $C_1$-$C_4$ alcohol, and, in particular, ethanol or isopropanol. The agents according to the invention may additionally include further organic solvents, such as for example 4-methoxybutanol, ethyl diglycol, 1,2-propylene glycol, n-propanol, n-butanol, n-butylene glycol, glycerol, diethylene glycol monoethyl ether and diethylene glycol mono-n-butyl ether. Any water-soluble organic solvents are preferred for this purpose. Preferred agents according to the invention are characterized in that they additionally include a nonaqueous solvent, wherein preferred agents according to the invention include the solvent in a concentration of 0.1 to 30 wt. %, preferably in a concentration of 1 to 20 wt. %, particularly preferably in a concentration of 2 to 10 wt. %, in each case relative to the agent.

Examples of the substituents R1, R2, R3, R4, R5, R6, R7 and R8 stated in the formula (I) are stated by way of example. Examples of $C_1$-$C_6$ alkyl groups are —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$(CH_2)_4CH_3$, and —$(CH_2)_5CH_3$. Particularly preferred alkyl residues are methyl and ethyl. Examples of $C_2$-$C_6$ alkenyl groups are vinyl, prop-2-enyl(allyl), 2-methylprop-2-enyl, but-3-enyl, but-2-enyl, pent-4-enyl, or pent-3-enyl. Examples of $C_2$-$C_6$ hydroxyalkyl groups are —$CH_2CH_2OH$, —$CH_2CH_2CH_2OH$, —$CH_2CH(OH)CH_3$, and —$CH_2CH_2CH_2CH_2OH$, wherein the group —$CH_2CH_2OH$ is preferred. Examples of $C_2$-$C_6$ polyhydroxyalkyl groups are 1,2-dihydroxyethyl, 2,3-dihydroxypropyl, 3,4-dihydroxybenzyl, and 2,4-dihydroxybenzyl. Examples of $C_1$-$C_6$ alkoxy groups are methoxy and ethoxy, preferably methoxy. Examples of halogen are fluorine, chlorine, bromine, and iodine, wherein chlorine and bromine are preferred. Examples of cyano-$C_1$-$C_6$-alkyl groups are cyanomethyl, and 2-cyanoethyl. Examples of aryl-$C_1$-$C_6$-alkyl groups are phenylmethyl(benzyl), 2-phenylethyl, and 1-phenylethyl. The residues R1 and R2 and/or the residues R4 and R5 may form, providing they are in ortho position relative to one another, a 5- or 6-membered, saturated or unsaturated, carbocyclic, or heterocyclic ring. One example of an unsaturated carbocyclic ring is benzene. Examples of saturated carbocyclic rings are cyclohexane and cyclopentane. Examples of unsaturated heterocyclic rings are pyridine, pyrimidine, pyrazine, pyridazine, pyrrole, imidazole, furan, and thiophene. Examples of saturated heterocyclic rings are pyrrolidine, piperidine, morpholine, 1,4-dioxane, and tetrahydrofuran. Examples of an alkylsulfonyl group are methylsulfonyl, ethylsulfonyl, and propylsulfonyl.

Structures according to the invention of the general formula (I) have a heterocycle A which bears a quaternary nitrogen atom and thus a positive charge. The compounds of the general formula (I) furthermore have a sulfuric acid ester grouping attached via Y to the chromophoric system. The two charges present within the molecule are thus neutralized and the dye assumes zwitterionic form, forming an internal salt.

Preferred residues A are thiazolium groups (II), imidazolium groups (III), 1,2,4-triazolium groups (IV), 1,3,4-thiadiazolium groups (VI), 1,2,4-thiadiazolium groups (VII), benzimidazolium groups (IX), benzothiazolium groups (X), and the pyridinium groups (XII) and (XIII). Within this group of preferred residues A, groups (II), (III), (IV), (VII), (X), (XII), and (XIII) are distinguished by particularly good coloring characteristics and are therefore more preferred. It is explicitly particularly preferred for the residue A to denote one of groups (II), (III), (IV), (VII) or (X).

A further embodiment of the first subject matter of the invention is an agent according to the invention which is characterized in that it includes at least one compound of the formula (I), in which A denotes one of structures (II), (III), (IV), (VI), (VII), (IX), (X), (XII) or (XIII), preferably one of structures (II), (III), (IV), (VII), (X), (XII) or (XIII), and more preferably one of structures (II), (III), (IV), (VII) or (X).

It is furthermore preferred for X to denote a group N—R3. Y advantageously denotes $(CH_2)_n$ with n equal to 2 or 3.

A further embodiment of the first subject matter of the invention is an agent according to the invention which is characterized in that it includes at least one compound of the formula (I) in which X denotes N—R3 and Y denotes $(CH_2)_n$ with n equal to 2 or 3.

The agents according to the invention may include compounds of the formula (I) in which X denotes N—R3. With R3 equal to the group —Y'—O—$SO_2$—OM, the compounds of the formula (I) may also include a second sulfuric acid ester grouping. However, compounds of the formula (I) which are preferred according to the invention include only one sulfuric acid ester grouping. X preferably denotes N—R3 and R3 denotes a $C_1$-$C_6$ alkyl group or a $C_2$-$C_6$ alkenyl group, preferably a $C_1$-$C_6$ alkyl group, and more preferably a methyl or an ethyl group.

A further embodiment of the first subject matter of the invention is an agent according to the invention which is characterized in that it includes at least one compound of the formula (I), in which X denotes N—R3 and R3 denotes a $C_1$-$C_6$ alkyl group or a $C_2$-$C_6$ alkenyl group, preferably a $C_1$-$C_6$ alkyl group, and more preferably a methyl or an ethyl group.

The residues R1 and R2 furthermore mutually independently preferably denote hydrogen, a $C_1$-$C_6$ alkyl group, a $C_1$-$C_6$ alkoxy group or halogen. R1 and R2 more preferably mutually independently denote hydrogen or a $C_1$-$C_6$ alkyl group, and more preferably in each case denote hydrogen.

A further embodiment of the first subject matter of the invention is thus an agent according to the invention which is characterized in that it includes at least one compound of the formula (I), in which R1 and R2 mutually independently denote hydrogen, a $C_1$-$C_6$ alkyl group, a $C_1$-$C_6$ alkoxy group or halogen, preferably mutually independently denote hydrogen or a $C_1$-$C_6$ alkyl group, and more preferably in each case denote hydrogen.

Including A, the compounds of the general formula (I) according to the invention include cationic heterocycles which are ring-substituted with the substituents R4 and optionally R5. Compounds in which R4 and optionally R5 mutually independently denote hydrogen, a $C_1$-$C_6$ alkyl group, a $C_1$-$C_6$ alkoxy group, halogen, a $C_1$-$C_6$ alkylsulfonyl group or a nitrile group are particularly suitable with regard to the object of the invention.

The groupings A are cationic and in each case include a quaternary nitrogen atom which is substituted with the residue R6. A further nitrogen atom present in the heterocycle optionally bears the residue R7. The residues R6 and, optionally, R7 are preferably mutually independently a $C_1$-$C_6$ alkyl group, and more preferably in each case a methyl group.

The residue R8 preferably denotes hydrogen or a $C_1$-$C_6$ alkyl group, and more preferably hydrogen or a methyl group.

According to the invention, the anionic sulfuric acid ester grouping is preferably neutralized by M. Compounds in which M represents a proton ($H^+$) or an alkali metal cation, in particular sodium or potassium ($Na^+$, $K^+$), achieve the object of the invention particularly effectively and are therefore preferred.

Agents for coloring keratinic fibers which are preferred according to the invention are characterized in that they include at least one compound of the formula (I) which is selected from:

2-(methyl{4-[(3-methyl-1,3-thiazol-3-ium-2-yl)diazenyl]phenyl}amino)ethyl sulfate,

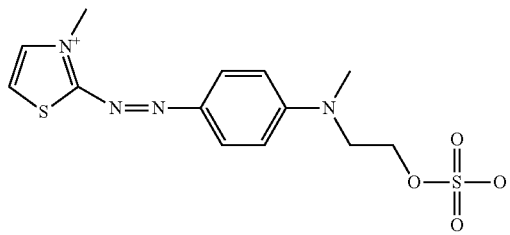 [SMILES: CN(CCOS(=O)(=O)O)c1ccc(N=Nc2scc[n+]2C)cc1]

2-(ethyl{4-[(3-methyl-1,3-thiazol-3-ium-2-yl)diazenyl]phenyl}amino)ethyl sulfate,

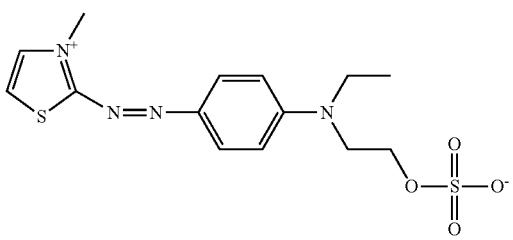 [SMILES: CCN(CCOS(=O)(=O)[O-])c1ccc(N=Nc2scc[n+]2C)cc1]

3-(methyl{4-[(3-methyl-1,3-thiazol-3-ium-2-yl)diazenyl]phenyl}amino)propyl sulfate,

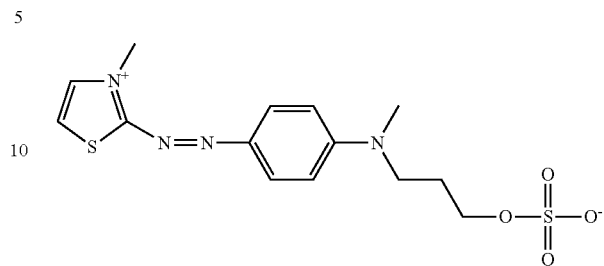

3-(ethyl{4-[(3-methyl-1,3-thiazol-3-ium-2-yl)diazenyl]phenyl}amino)propyl sulfate,

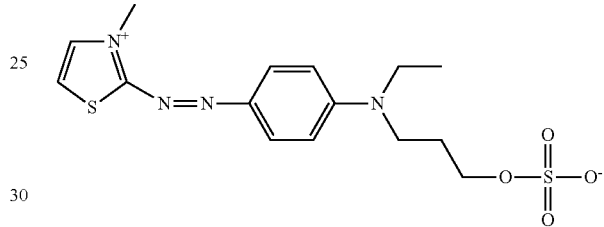

2-(methyl{3-methyl-4-[(3-methyl-1,3-thiazol-3-ium-2-yl)diazenyl]phenyl}amino)-ethyl sulfate,

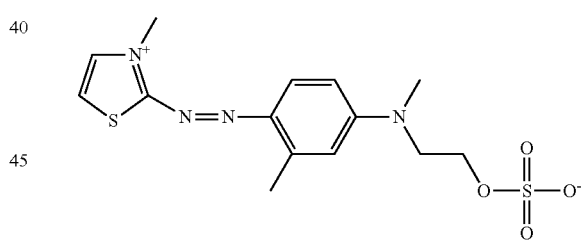

3-(ethyl{3-methyl-4-[(3-methyl-1,3-thiazol-3-ium-2yl)diazenyl]phenyl}amino)propyl sulfate,

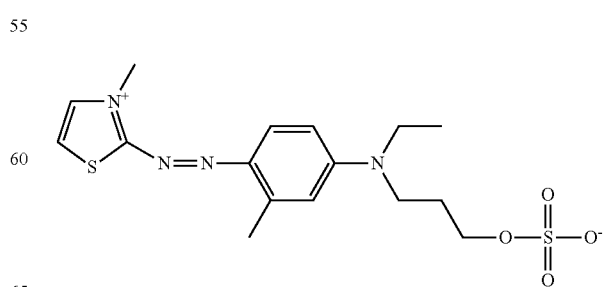

2-[{4-[(1,3-dimethyl-1H-imidazol-3-ium-2-yl)diazenyl]phenyl}(methyl)amino]ethyl sulfate,

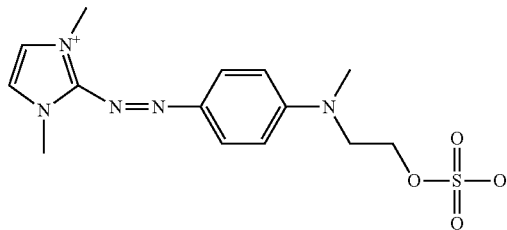 [SMILES: CN(CCOS(=O)(=O)O)c1ccc(N=Nc2n(C)cc[n+]2C)cc1]

2-[{4-[(1,3-dimethyl-1H-imidazol-3-ium-2-yl)diazenyl]phenyl}(ethyl)amino]ethyl sulfate,

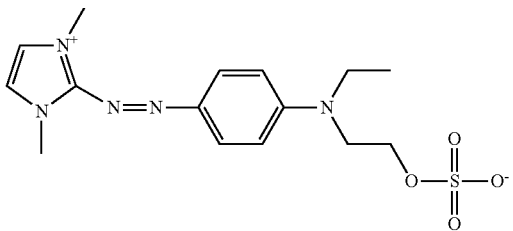 [SMILES: CCN(CCOS(=O)(=O)[O-])c1ccc(N=Nc2n(C)cc[n+]2C)cc1]

3-[{4-[(1,3-dimethyl-1H-imidazol-3-ium-2-yl)diazenyl]phenyl}(ethyl)amino]propyl sulfate,

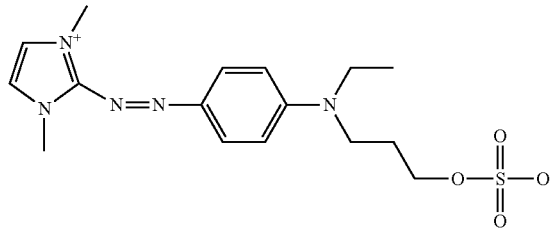 [SMILES: CCN(CCCOS(=O)(=O)O)c1ccc(N=Nc2n(C)cc[n+]2C)cc1]

2-[{4-[(1,3-dimethyl-1H-imidazol-3-ium-2-yl)diazenyl]-3-methylphenyl}(ethyl)amino]ethyl sulfate,

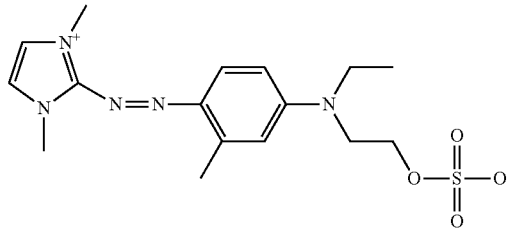 [SMILES: CCN(CCOS(=O)(=O)O)c1ccc(N=Nc2n(C)cc[n+]2C)c(C)c1]

3-[{4-[(1,3-dimethyl-1H-imidazol-3-ium-2-yl)diazenyl]-3-methylphenyl}(ethyl)amino]propyl sulfate,

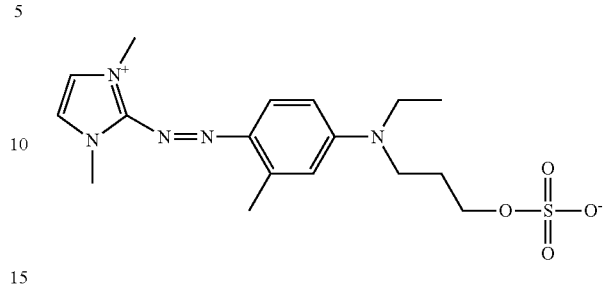

2-[{4-[(1,4-dimethyl-4H-1,2,4-triazol-1-ium-5-yl)diazenyl]phenyl}(methyl)amino]ethyl sulfate,

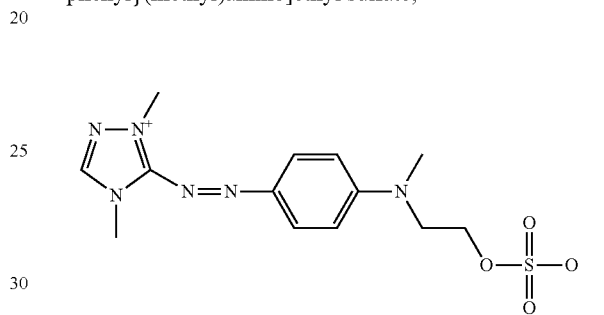

2-[{4-[(1,4-dimethyl-4H-1,2,4-triazol-1-ium-5-yl)diazenyl]phenyl}(ethyl)amino]ethyl sulfate,

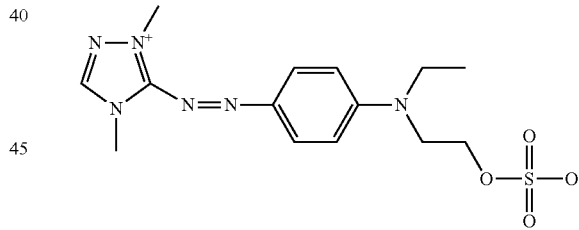

3-[{4-[(1,4-dimethyl-4H-1,2,4-triazol-1-ium-5-yl)diazenyl]phenyl}(ethyl)amino]propyl sulfate,

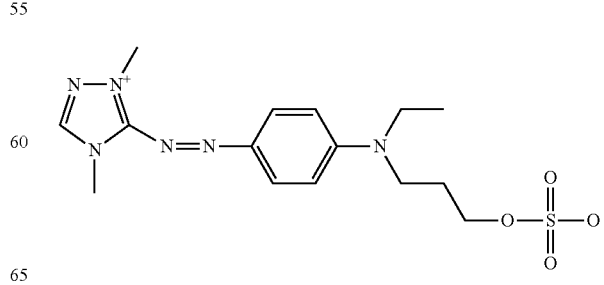

3-[{4-[(1,4-dimethyl-4H-1,2,4-triazol-1-ium-5-yl)diaz-
enyl]-3-methylphenyl}(methyl)amino]propyl sulfate, 3-(ethyl{4-[(3-methyl-1,3,4-thiadiazol-3-ium-2-yl)diaz-
enyl]phenyl}amino)propyl sulfate,

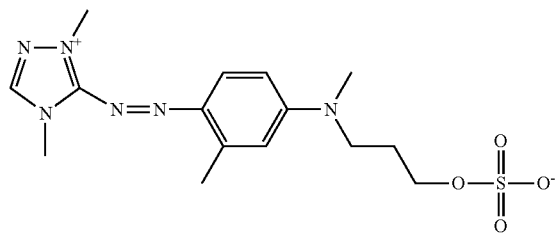 [SMILES: Cc1cc(N(C)CCCOS(=O)(=O)[O-])ccc1N=Nc1n(C)cn[n+]1C]

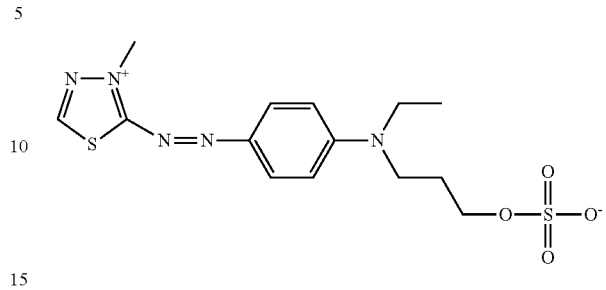

3-[{4-[(1,4-dimethyl-4H-1,2,4-triazol-1-ium-5-yl)diaz-
enyl]-3-methylphenyl}(ethyl)amino]propyl sulfate, 3-(methyl{3-methyl-4-[(3-methyl-1,3,4-thiadiazol-3-ium-2-
yl)diazenyl]phenyl}amino)propyl sulfate,

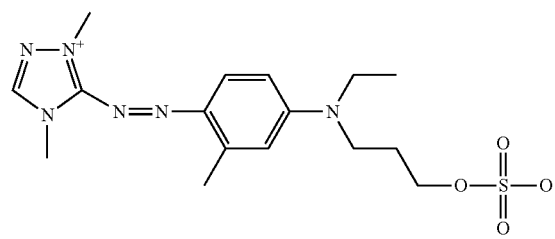 [SMILES: CCN(CCCOS(=O)(=O)O)c1ccc(N=Nc2n(C)cn[n+]2C)c(C)c1]

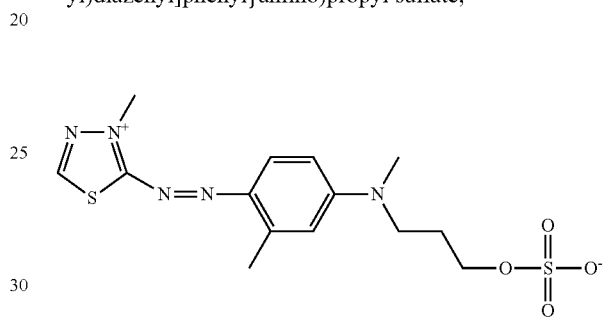

2-(methyl{4-[(3-methyl-1,3,4-thiadiazol-3-ium-2-yl)diaz-
enyl]phenyl}amino)ethyl sulfate, 3-(ethyl{3-methyl-4-[(3-methyl-1,3,4-thiadiazol-3-ium-2-
yl)diazenyl]phenyl}amino)propyl sulfate

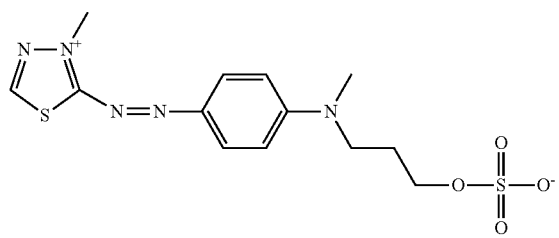

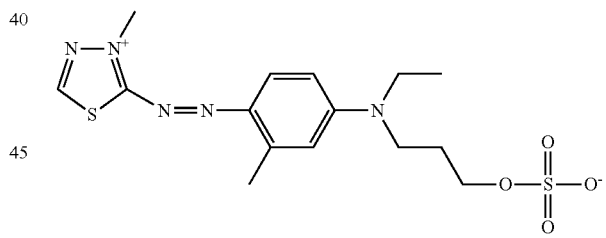

2-(ethyl{4-[(3-methyl-1,3,4-thiadiazol-3-ium-2-yl)diaz-
enyl]phenyl}amino)ethyl sulfate, 2-(methyl{4-[(4-methyl-1,2,4-thiadiazol-4-ium-5-yl)diaz-
enyl]phenyl}amino)ethyl sulfate,

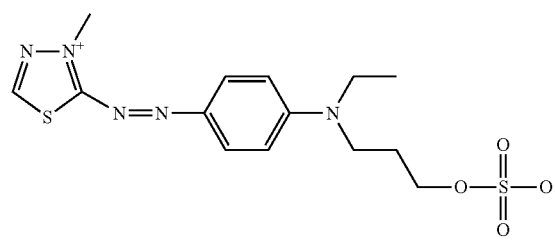

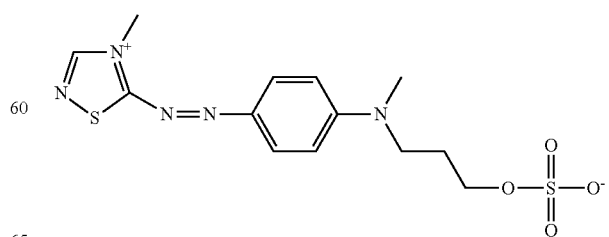

2-(ethyl{4-[(4-methyl-1,2,4-thiadiazol-4-ium-5-yl)diaz-
  enyl]phenyl}amino)ethyl sulfate,

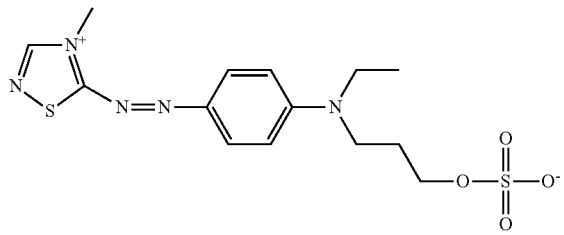 [SMILES: CCN(CCCOS(=O)(=O)[O-])c1ccc(N=Nc2snc[n+]2C)cc1]

3-(ethyl{4-[(4-methyl-1,2,4-thiadiazol-4-ium-5-yl)diaz-
  enyl]phenyl}amino)propyl sulfate,

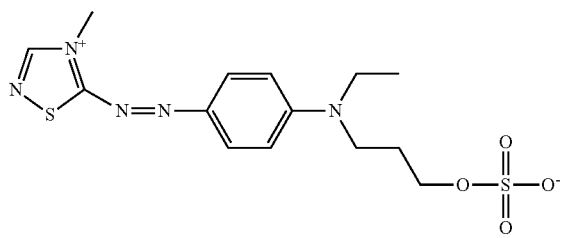

2-(methyl{3-methyl-4-[(4-methyl-1,2,4-thiadiazol-4-ium-5-
  yl)diazenyl]phenyl}amino)ethyl sulfate,

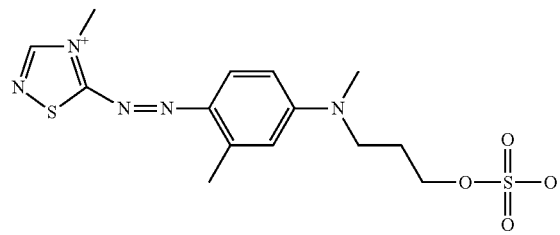

3-(ethyl{3-methyl-4-[(4-methyl-1,2,4-thiadiazol-4-ium-5-
  yl)diazenyl]phenyl}amino)propyl sulfate,

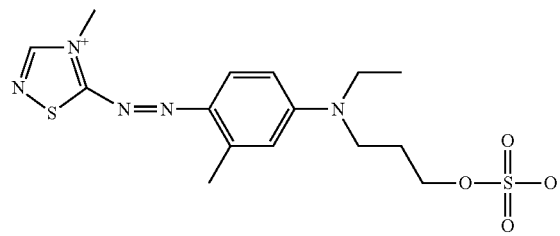 [SMILES: Cc1cc(N(C)CCCOS(=O)(=O)O)ccc1N=Nc1snc[n+]1C]

2-(methyl{4-[(3-methyl-1,3-benzothiazol-3-ium-2-yl)diaz-
  enyl]phenyl}amino)ethyl sulfate,

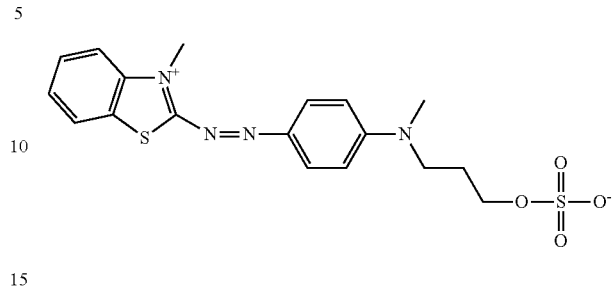

2-(ethyl{4-[(3-methyl-1,3-benzothiazol-3-ium-2-yl)diaz-
  enyl]phenyl}amino)ethyl sulfate,

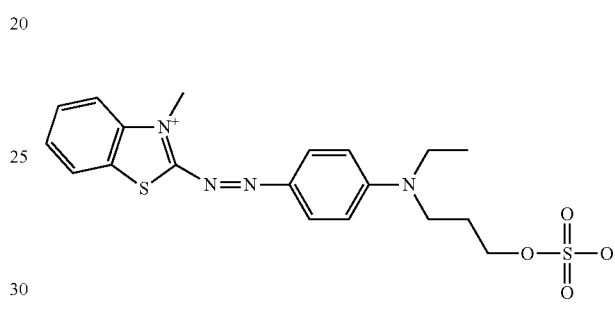

2-(ethyl{4-[(3,6-dimethyl-1,3-benzothiazol-3-ium-2-yl)dia-
  zenyl]phenyl}amino)ethyl sulfate,

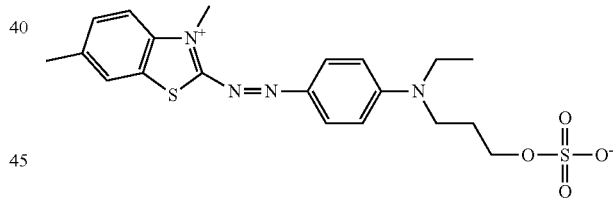

3-(ethyl{4-[(3-methyl-1,3-benzothiazol-3-ium-2-yl)diaz-
  enyl]phenyl}amino)propyl sulfate,

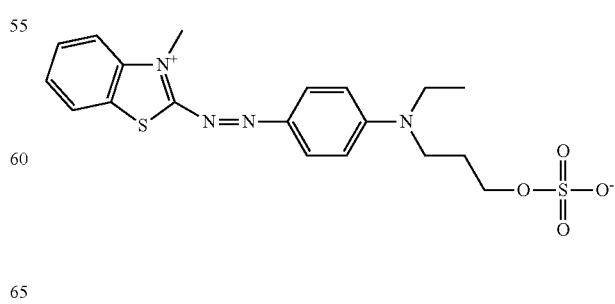

2-(methyl{3-methyl-4-[(3-methyl-1,3-benzothiazol-3-ium-2-yl)diazenyl]phenyl}amino)ethyl sulfate,

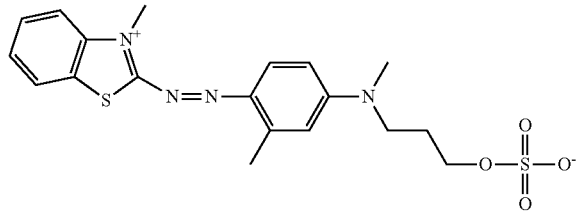 [SMILES: Cc1cc(N(C)CCCOS(=O)(=O)[O-])ccc1N=Nc1sc2ccccc2[n+]1C]

3-(ethyl{3-methyl-4-[(3-methyl-1,3-benzothiazol-3-ium-2-yl)diazenyl]phenyl}amino)propyl sulfate,

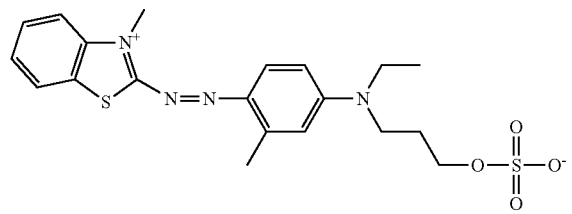 [SMILES: CCN(CCCOS(=O)(=O)[O-])c1ccc(N=Nc2sc3ccccc3[n+]2C)c(C)c1]

2-[{4-[(1,3-dimethyl-1H-benzimidazol-3-ium-2-yl)diazenyl]phenyl}(methyl)amino]ethyl sulfate,

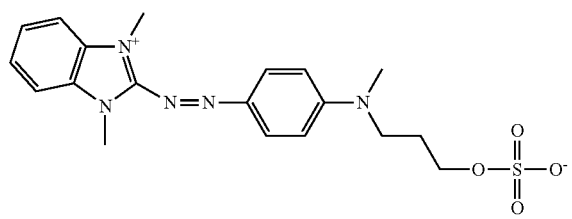 [SMILES: CN(CCCOS(=O)(=O)[O-])c1ccc(N=Nc2n(C)c3ccccc3[n+]2C)cc1]

2-[{4-[(1,3-dimethyl-1H-benzimidazol-3-ium-2-yl)diazenyl]phenyl}(ethyl)amino]ethyl sulfate,

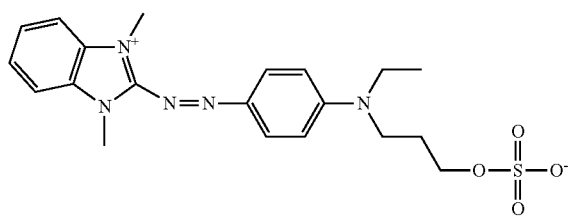

3-[{4-[(1,3-dimethyl-1H-benzimidazol-3-ium-2-yl)diazenyl]phenyl}(ethyl)amino]propyl sulfate,

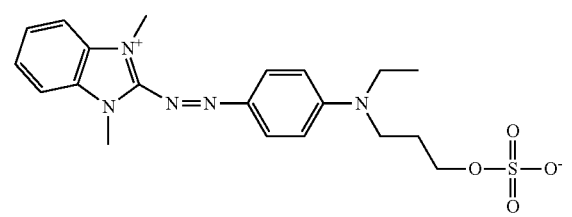 [SMILES: CCN(CCCOS(=O)(=O)[O-])c1ccc(N=Nc2n(C)c3ccccc3[n+]2C)cc1]

2-[{4-[(1,3-dimethyl-1H-benzimidazol-3-ium-2-yl)diazenyl]-3-methylphenyl}(methyl)amino]ethyl sulfate,

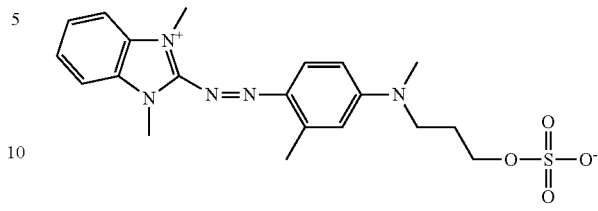

3-[{4-[(1,3-dimethyl-1H-benzimidazol-3-ium-2-yl)diazenyl]-3-methylphenyl}(ethyl)amino]propyl sulfate,

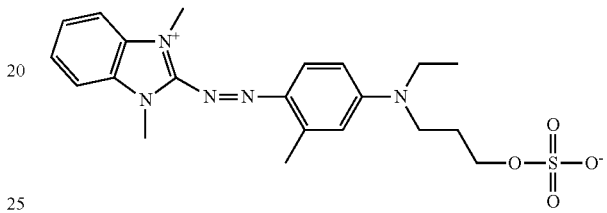

An explicitly more preferred embodiment of the first subject matter of the invention are agents which include at least one compound of the formula (I) which is selected from:
2-(methyl{4-[(3-methyl-1,3-thiazol-3-ium-2-yl)diazenyl]phenyl}amino)ethyl sulfate;
2-(ethyl{4-[(3-methyl-1,3-thiazol-3-ium-2-yl)diazenyl]phenyl}amino)ethyl sulfate;
2-[{4-[(1,3-dimethyl-1H-imidazol-3-ium-2-yl)diazenyl]phenyl}(methyl)amino]ethyl sulfate;
2-[{4-[(1,3-dimethyl-1H-imidazol-3-ium-2-yl)diazenyl]phenyl}(ethyl)amino]ethyl sulfate;
2-[{4-[(1,4-dimethyl-4H-1,2,4-triazol-1-ium-5-yl)diazenyl]phenyl}(methyl)amino]ethyl sulfate;
2-[{4-[(1,4-dimethyl-4H-1,2,4-triazol-1-ium-5-yl)diazenyl]phenyl}(ethyl)amino]ethyl sulfate;
3-[{4-[(1,4-dimethyl-4H-1,2,4-triazol-1-ium-5-yl)diazenyl]phenyl}(ethyl)amino]propyl sulfate;
2-(methyl{4-[(3-methyl-1,3,4-thiadiazol-3-ium-2-yl)diazenyl]phenyl}amino)ethyl sulfate;
2-(ethyl{4-[(3-methyl-1,3,4-thiadiazol-3-ium-2-yl)diazenyl]phenyl}amino)ethyl sulfate;
2-(methyl{4-[(4-methyl-1,2,4-thiadiazol-4-ium-5-yl)diazenyl]phenyl}amino)ethyl sulfate;
2-(ethyl{4-[(4-methyl-1,2,4-thiadiazol-4-ium-5-yl)diazenyl]phenyl}amino)ethyl sulfate;
2-(methyl{4-[(3-methyl-1,3-benzothiazol-3-ium-2-yl)diazenyl]phenyl}amino)ethyl sulfate;
2-(methyl{4-[(3,6-dimethyl-1,3-benzothiazol-3-ium-2-yl)diazenyl]phenyl}amino)ethyl sulfate; and
2-(ethyl{4-[(3-methyl-1,3-benzothiazol-3-ium-2-yl)diazenyl]phenyl}amino)ethyl sulfate.

The agents according to the invention for coloring keratinic fibers preferably include the compound(s) of the formula (I) in quantities of above 1 ppm and below 10 wt. %, in each case relative to the entire agent. A preferred embodiment of the first subject matter of the invention is here an agent which is characterized in that it includes the compound(s) of the formula (I) in each case in a quantity of 0.001 to 5 wt. %, preferably of 0.025 to 2.5 wt. %, more preferably of 0.05 to 2.0 wt. %, and more preferably of 0.1 to 1.5 wt. %, in each case relative to the total weight of the agent.

In a further preferred embodiment, the agents according to the invention additionally include, in addition to the compound of the formula (I), at least one further substantive dye. Substantive dyes may be subdivided into anionic, cationic and nonionic substantive dyes. The substantive dyes are preferably selected from nitrophenylenediamines, nitroaminophenols, azo dyes, anthraquinones, indophenols or triarylmethanes and the physiologically acceptable salts thereof. The additional substantive dyes are in each case preferably used in a proportion of 0.001 to 2 wt. %, relative to the total weight of the agent.

Preferred anionic substantive dyes are the compounds known by the international names or trade names bromophenol blue, tetrabromophenol blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, and Acid Black 52.

Preferred cationic substantive dyes are Basic Blue 7, Basic Blue 26, Basic Violet 2, Basic Violet 14, Basic Yellow 57, Basic Red 76, Basic Blue 16, Basic Blue 347 (Cationic Blue 347/Dystar), HC Blue 16, Basic Blue 99, Basic Brown 16 and Basic Brown 17 and Yellow 87, Basic Orange 31, and Basic Red 51.

Suitable nonionic substantive dyes are in particular nonionic nitro and quinone dyes and neutral azo dyes. Preferred nonionic substantive dyes are the compounds known by the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenol)amino]-benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid, and 2-chloro-6-ethylamino-4-nitrophenol.

It is not necessary for the optionally present substantive dyes in each case to be uniform compounds. Instead, as a result of the production processes for the individual dyes, subordinate quantities of still further components may be present, provided that these do not have a disadvantageous effect on the coloring result or have to be excluded for other, for example toxicological, reasons.

The coloring agents may furthermore be used as lightening coloring agents. In order to achieve the lightening effect, the agents include to this end hydrogen peroxide and/or one of the solid addition products thereof onto organic or inorganic compounds. Examples of such addition products are addition products onto urea, melamine, and sodium borate.

In order to achieve an enhanced brightening and bleaching action, the agent may furthermore include at least one peroxo salt. Suitable peroxo salts are inorganic peroxo compounds, preferably selected from ammonium peroxodisulfate, alkali metal peroxodisulfates, ammonium peroxomonosulfate, alkali metal peroxomonosulfates, alkali metal peroxodiphosphates, and alkaline earth metal peroxides. More preferred peroxodisulfates are sodium persulfate, potassium persulfate, and ammonium persulfate.

A further embodiment of the first subject matter of the invention is therefore an agent for coloring and simultaneously lightening keratinic fibers that is characterized in that it additionally includes at least one oxidizing agent, selected from hydrogen peroxide, one of the solid addition products thereof onto organic or inorganic compounds, sodium persulfate, potassium persulfate, and ammonium persulfate.

In a preferred embodiment, hydrogen peroxide itself is used as an aqueous solution. The concentration of a hydrogen peroxide solution in the agent according to the invention is determined on the one hand by statutory requirements and on the other hand by the desired effect; 6 to 12 wt. % solutions in water are preferably used.

Ready-to-use agents of the first subject matter of the invention which are preferred according to the invention are characterized in that they include 0.5 to 15 wt. %, preferably 1 to 12.5 wt. %, more preferably 2.5 to 10 wt. %, and, in particular, 3 to 6 wt. % hydrogen peroxide, in each case relative to the total weight of the agent.

If the agents additionally include persulfates, said persulfates are present in the agent preferably in a quantity of 1.5 to 60 wt. %, preferably of 2.0 to 45 wt. %, more preferably of 2.5 to 40 wt. %, and, in particular, of 5 to 30 wt. %, in each case relative to the total weight of the agent.

The agent may include further bleach boosters in order to boost blonding action, such as for example tetraacetylethylenediamine (TAED), 1,5-diacetyl-2,4-dioxohexahydro-1,3,5-triazine (DADHT), tetraacetylglycoluril (TAGU), N-nonanoylsuccinimide (NOSI), n-nonanoyl- or isononanoyloxybenzenesulfonate (n- or i-NOBS), phthalic anhydride, triacetin, ethylene glycol diacetate and 2,5-diacetoxy-2,5-dihydrofuran, and carbonate salts or hydrogencarbonate salts, in particular, ammonium hydrogencarbonate, ammonium carbonate, sodium hydrogencarbonate, disodium carbonate, potassium hydrogencarbonate, dipotassium carbonate and calcium carbonate, and nitrogen—including, heterocyclic bleach boosters, such as 4-acetyl-1-methylpyridinium p-toluenesulfonate, 2-acetyl-1-methylpyridinium p-toluenesulfonate, and N-methyl-3,4-dihydroisoquinolinium p-toluenesulfonate.

Lightening may be further increased by additionally adding at least one $SiO_2$ compound, such as silica or silicates, in particular water glasses, to the composition according to the invention. It may be preferred according to the invention to use the $SiO_2$ compounds in quantities of 0.05 wt. % to 15 wt. %, more preferably in quantities of 0.15 wt. % to 10 wt. %, and particularly preferably in quantities of 0.2 wt. % to 5 wt. %, in each case relative to the anhydrous composition, according to the invention. The stated quantities here in each case indicate the content of $SiO_2$ compounds, excluding their water content, in the agents.

It has furthermore proved advantageous for the coloring agents, in particular, if they additionally include hydrogen peroxide, to include at least one stabilizer or complexing agent. More preferred stabilizers are phenacetin, alkali metal benzoates (sodium benzoate), and salicylic acid. Any prior art complexing agents may furthermore be used. Complexing agents which are preferred according to the invention are nitrogen—including polycarboxylic acids, in particular Ethylenediaminetetraacidic acid (EDTA) and Ethylenediamine-N,N'-disuccinic acid (EDDS), and phosphonates, in particular 1-hydroxyethane-1,1-diphosphonate (HEDP) and/or ethylenediaminetetramethylenephosphonate (EDTMP) and/or diethylenetriaminepentamethylenephosphonate (DTPMP), or the sodium salts thereof.

The agents according to the invention may furthermore also be used as oxidation coloring agents. Such oxidation coloring agents additionally include at least one oxidation dye precursor, preferably at least one oxidation dye precursor of the developer type and at least one oxidation dye precursor of the coupler type. Particularly suitable oxidation dye precursors of the developer type are here selected from p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4'-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-diamino-4,5,6-triaminopyrimidine and 2,3-diamino-6,7-dihydro-1H,5H-pyrazolo[1,2-a]pyrazol-1-one, and the physiologically acceptable salts thereof.

Particularly suitable oxidation dye precursors of the coupler type are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis-(2,4-diaminophenoxy)propane, 1-methoxy-2-amino-4-(2-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline and 7-hydroxyindoline, the physiologically acceptable salts thereof, or mixtures of these compounds.

The developer components and coupler components are preferably used in a quantity of 0.0001 to 5.0 wt. %, preferably 0.001 to 2.5 wt. %, in each case relative to the weight of the ready-to-use agent. Developer components and coupler components are generally used in approximately molar quantities relative to one another. While molar use has also proven convenient, a certain excess of individual oxidation dye precursors is not disadvantageous, such that developer components and coupler components may be present in a molar ratio of 1:0.5 to 1:3, in particular 1:1 to 1:2.

In the case of oxidation coloring agents, the agents preferably include an oxidizing agent, preferably hydrogen peroxide. The quantities of hydrogen peroxide correspond to the quantities in the lightening agents according to the invention.

The ready-to-use coloring agents may furthermore include additional active ingredients, auxiliary substances and additives in order to improve coloring performance and adjust further desired properties of the agents.

The ready-to-use coloring agents are preferably provided as a liquid preparation and a surface-active substance is therefore additionally added to the agents, wherein such surface-active substances, depending on the area of application are described as surfactants or as emulsifiers: they are preferably selected from anionic, cationic, zwitterionic, amphoteric and nonionic surfactants and emulsifiers.

Agents which are preferred according to the invention are characterized in that the agent additionally includes at least one anionic surfactant. Preferred anionic surfactants are fatty acids, alkyl sulfates, alkyl ether sulfates and ether carboxylic acids with 10 to 20 C atoms in the alkyl group, and up to 16 glycol ether groups per molecule. The anionic surfactants are used in proportions of 0.1 to 45 wt. %, preferably of 1 to 30 wt. % and particularly preferably of 1 to 15 wt. %, relative to the total quantity of the ready-to-use agent.

Agents which are preferred according to the invention are characterized in that the agent additionally includes at least one zwitterionic surfactant. Particularly suitable zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethylimidazolines. One preferred zwitterionic surfactant is known by the International Nomenclature of Cosmetic Ingredients (INCI) name Cocamidopropyl Betaine.

Agents which are preferred according to the invention are characterized in that the agent additionally includes at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids. Particularly preferred amphoteric surfactants are N-cocoalkyl aminopropionate, cocoacylaminoethyl aminopropionate, and $C_{12}$-$C_{18}$ acyl sarcosine.

It has furthermore proved advantageous for the agents to include further non-ionogenic interfacially active substances. Preferred nonionic surfactants have proved to be alkyl polyglycosides together with alkylene oxide addition products onto fatty alcohols and fatty acids with in each case 2 to 30 mol of ethylene oxide per mol of fatty alcohol or fatty acid, respectively. Preparations having excellent properties are likewise obtained if they include fatty acid esters of ethoxylated glycerol as the nonionic surfactants.

The nonionic, zwitterionic or amphoteric surfactants are used in proportions of 0.1 to 45 wt. %, preferably of 1 to 30 wt. % and particularly preferably of 1 to 15 wt. %, relative to the total quantity of the ready-to-use agents.

Agents which are suitable according to the invention may also include cationic surfactants of the quaternary ammonium compound, ester quat and amidoamine type. Preferred quaternary ammonium compounds are ammonium halides, and the imidazolium compounds known under the INCI names Quaternium-27 and Quaternium-83. Quaternized protein hydrolysates are further cationic surfactants which are usable according to the invention. One compound from the group of amidoamines which is particularly suitable according to the invention is stearamidopropyldimethylamine which is commercially available under the name TEGO AMID S 18 developed and distributed by Evonik Industries. Preferred ester quats are quaternized ester salts of fatty acids with triethanolamine, quaternized ester salts of fatty acids with diethanolalkylamines, and quaternized ester salts of fatty acids with 1,2-dihydroxypropyldialkylamines. The agents used according to the invention preferably include the cationic surfactants in proportions of 0.05 to 10 wt. %, relative to the total agent.

The ready-to-use coloring agents may include further auxiliary substances and additives. It has for instance proved advantageous for the agent to include at least one thickener. No restrictions apply in principle with regard to these thickeners. Both organic and purely inorganic thickeners may be used.

Suitable thickeners are anionic, synthetic polymers; cationic, synthetic polymers; naturally occurring thickeners, such as nonionic guar gums, scleroglucan gums or xanthan gums, gum arabic, gum ghatti, karaya gum, tragacanth gum, carrageenan gum, agar-agar, locust bean flour, pectins, alginates, starch fractions and derivatives such as amylose, amylopectin and dextrins, and cellulose derivatives, such as for example methylcellulose, carboxyalkylcelluloses and hydroxyalkylcelluloses; nonionic, synthetic polymers such polyvinyl alcohol or polyvinylpyrrolidinone; as well as inorganic thickeners, in particular phyllosilicates such as for example bentonite, in particular smectites, such as montmorillonite or hectorite.

Coloring processes on keratin fibers conventionally proceed in an alkaline environment. Establishing an excessively high pH value is, however, not desirable if the keratin fibers and also the skin are to be treated as gently as possible. It is therefore preferred for the pH value of the ready-to-use agent to be between 6 and 11, in particular between 7 and 10.5. The pH values for the purposes of the present invention are pH values which were measured at a temperature of 22° C.

Alkalizing agents usable according to the invention for establishing the preferred pH value may be selected from the group formed of ammonia, alkanolamines, basic amino acids, together with inorganic alkalizing agents such as alkaline earth) metal hydroxides, alkali(ne earth) metal metasilicates, alkali(ne earth) metal phosphates, and alkali(ne earth) metal hydrogenphosphates. Preferred inorganic alkalizing agents are magnesium carbonate, sodium hydroxide, potassium hydroxide, sodium silicate and sodium metasilicate. Organic alkalizing agents usable according to the invention are preferably selected from monoethanolamine, 2-amino-2-methyl-propanol and triethanolamine. The basic amino acids usable as alkalizing agents according to the invention are preferably selected from the group formed by arginine, lysine, ornithine, and histidine, more preferably arginine.

The agents according to the invention may moreover include further active substances, auxiliary substances and additives, such as nonionic polymers (for example vinylpyrrolidinone/vinyl acrylate copolymers, polyvinylpyrrolidinone, vinylpyrrolidinone/vinyl acetate copolymers, polyethylene glycols and polysiloxanes;); silicones, such as volatile or non-volatile, straight-chain, branched or cyclic, crosslinked or uncrosslinked polyalkylsiloxanes (such as dimethicones or cyclomethicones), polyarylsiloxanes and/or polyalkylarylsiloxanes, in particular polysiloxanes with organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers); cationic polymers, such as quaternized cellulose ethers, polysiloxanes with quaternary groups, such as dimethyldiallylammonium chloride copolymers, dimethylaminoethylmethacrylate methosulfate-vinylpyrrolidinone copolymers quaternized with diethyl sulfate, vinylimidazolinium methochloride copolymers; zwitterionic and amphoteric polymers; anionic polymers such as for example polyacrylic acids or crosslinked polyacrylic acids; structuring agents such as glucose, maleic acid and lactic acid, hair-conditioning compounds, such as phospholipids, for example lecithin and cephalins; perfume oils, dimethyl isosorbide and cyclodextrins; active substances which improve fiber structure, in particular mono-, di- and oligosaccharides such as for example glucose, galactose, fructose, fruit sugar and lactose; dyes for coloring the agent; antidandruff active ingredients such as piroctone olamine, zinc omadine and climbazole; amino acids and oligopeptides; animal- or plant-based protein hydrolysates, as well as in the form of the fatty acid condensation products or optionally anionically or cationically modified derivatives thereof; vegetable oils; light stabilizers and UV blockers; active substances such as panthenol, pantothenic acid, pantolactone, allantoin, pyrrolidinone carboxylic acids and the salts thereof and bisabolol; polyphenols, in particular hydroxycinnamic acids, 6,7-dihydroxycoumarins, hydroxybenzoic acids, catechins, tannins, leucoanthocyanidines, anthocyanidines, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogencarbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3 distearate; pigments and propellants such as propane-butane mixtures, $N_2O$, dimethyl ether, $CO_2$, and air.

A person skilled in the art will select these further substances in accordance with the desired properties of the agents. With regard to further optional components and the quantities of these components used, reference is explicitly made to the relevant handbooks known to a person skilled in the art. The additional active ingredients and auxiliaries are preferably used in the agents according to the invention in quantities of in each case 0.0001 to 25 wt. %, in particular of 0.0005 to 15 wt. %, relative to the total weight of the mixture for use.

The present invention also provides the use of an agent according to the invention for coloring, or for coloring and simultaneously lightening keratinic fibers, for improving the intensity and brightness of the coloring, and/or for improving the fastness characteristics of the coloring, in particular washing fastness, light fastness and ultrablonding fastness.

The present invention further provides a method for coloring keratinic fibers, in particular human hair, which is characterized in that an agent of the first subject matter of the invention is applied onto the keratin—including fibers, left on the fibers for 5 to 60 minutes and then rinsed back out or washed out with a shampoo. The period of exposure for the ready-to-use coloring agent preferably amounts 5 to 45 min, in particular 10 to 40 min, and more preferably 15 to 35 min. During the period of exposure of the fiber to the agent it may be advantageous to assist the lightening process by supplying heat. Heat may be supplied by an external heat source, such as for example hot air from a hot air blower, and also, in particular when lightening the hair of a living test subject, by the body temperature of the test subject. In the case of the latter possibility, the part to be dyed is conventionally covered with a cap. Exposure at room temperature is likewise according to the invention. In particular, the temperature during the period of exposure is between 20° C. and 40° C., in particular between 25° C. and 38° C. After the end of the period of exposure, the remaining coloring preparation is rinsed out of the hair with water or a cleaning agent. Conventional commercial shampoo may in particular be used here as the cleaning agent, wherein it is in particular possible to dispense with the cleaning agent and carry out the rinsing operation with water if the lightening agent has a carrier with a high surfactant content.

The agents according to the invention may be formulated and correspondingly used as a single component agent (coloring and lightening agent) or as multicomponent agents such as two-component agents or three-component agents. Separation into multicomponent systems may in particular be considered where incompatibilities of the ingredients are to be expected or feared. In such systems, the agent for use is produced by the consumer directly before application by mixing the components.

A coloring and lightening method in which the lightening cream and the oxidizing agent are initially separate is here preferred. A preferred method according to the invention is therefore characterized in that a water-based composition including hydrogen peroxide is mixed with an agent according to the invention of the first subject matter of the invention to form a homogeneous composition and the latter is applied onto the hair.

The above statements regarding the agents according to the invention apply mutatis mutandis with regard to further preferred embodiments of the methods according to the invention.

The compounds of the general formula (I) are highly suitable as substantive dyes for hair coloring. Colorings are here obtained with elevated color intensity and color brightness and good fastness characteristics. It is also possible in this manner simultaneously to lighten and color hair, it being possible to achieve a bright color result even on dark hair.

Compounds of the general formula (I) are not hitherto known from the literature. The present invention accordingly also provides compounds of formula (I),

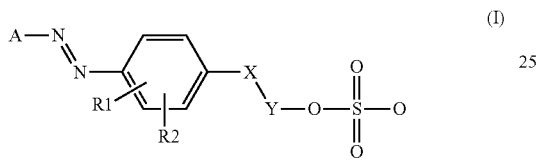
(I)

in which R1 and R2 mutually independently denote hydrogen, a $C_1$-$C_6$ alkyl group, a $C_2$-$C_6$ alkenyl group, a hydroxyl group, a $C_1$-$C_6$ alkoxy group, halogen, an amino group, an acetylamino group, a nitro group or a nitrile group. Alternatively, R1 and R2 form a 5- or 6-membered, saturated or unsaturated, carbocyclic or heterocyclic ring providing they are in ortho position relative to one another. X denotes O or N—R3. R3 denotes hydrogen, a $C_1$-$C_6$ alkyl group, a $C_2$-$C_6$ alkenyl group, a $C_2$-$C_6$ hydroxyalkyl group, a $C_2$-$C_6$ polyhydroxyalkyl group, a $C_1$-$C_6$ cyanoalkyl group, an aryl-$C_1$-$C_6$-alkyl group, or a group —Y'—O—$SO_2$—OM. Y and Y' in each case mutually independently denote $(CH_2)_n$ or $C_2H_4$—$(OC_2H_4)_n$ or $(CH_2)_n$—O—$(CH_2)_m$, or $(CH_2)_n$—N(R8)-$(CH_2)_m$, and n and optionally m in each case mutually independently denote an integer from 1 to 6. A denotes one of structures (II) to (XIII),

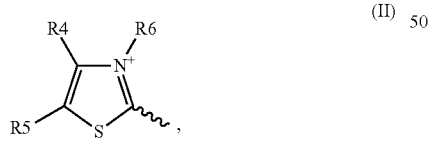
(II)

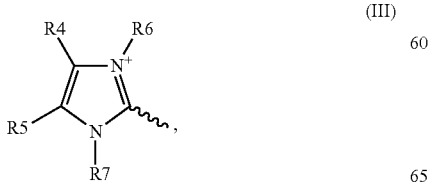
(III)

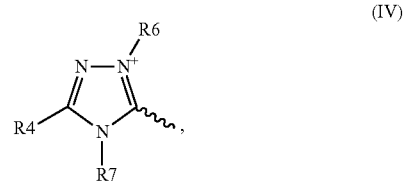
(IV)

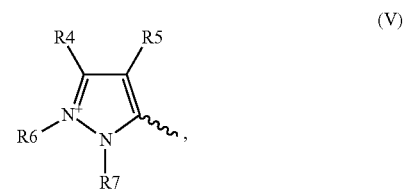
(V)

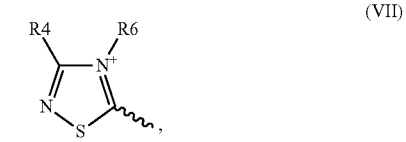
(VI)

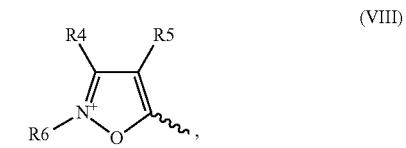
(VII)

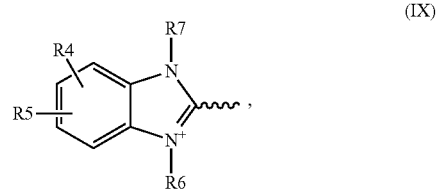
(VIII)

(IX)

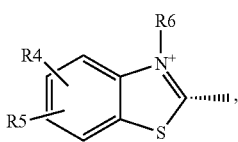
(X)

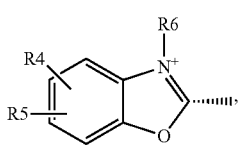
(XI)

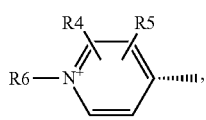
(XII)

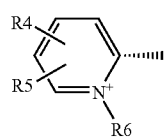
(XIII)

in which R4 and R5 in each case mutually independently denote hydrogen, a $C_1$-$C_6$ alkyl group, a $C_2$-$C_6$ alkenyl group, a hydroxyl group, a $C_1$-$C_6$ alkoxy group, halogen, an amino group, an acetylamino group, a $C_1$-$C_6$ alkylsulfonyl group, or a nitrile group. Alternatively, R4 and R5 form a 5- or 6-membered, saturated or unsaturated, carbocyclic or heterocyclic ring providing they are in ortho position relative to one another. R6 and R7 mutually independently denote a $C_1$-$C_6$ alkyl group, a $C_2$-$C_6$ alkenyl group or a $C_2$-$C_6$ hydroxyalkyl group. R8 denotes hydrogen, a $C_1$-$C_6$ alkyl group, a $C_2$-$C_6$ alkenyl group, or a $C_2$-$C_6$ hydroxyalkyl group, and M denotes hydrogen, an alkali metal, or half an equivalent of an alkaline earth metal.

The following examples are intended to illustrate the subject matter of the present application without limiting it in any way.

EXAMPLES

1. Synthesis Examples

Synthesis Example 1

This Example regards the synthesis of 2-(ethyl{4-[(3-methyl-1,3-thiazol-3-ium-2-yl)diazenyl]phenyl}amino)ethyl sulfate (substantive dye 1), and includes the synthesis of 2-[ethyl(phenyl)amino]ethyl hydrogensulfate. 16.5 g (0.10 mol) of 2-(N-ethylanilino)ethanol were added at a temperature of 35-40° C. to 25.0 ml of concentrated sulfuric acid. The reaction proceeded slightly exothermically and was kept within the stated temperature range by cooling with ice water. The mixture was stirred for a further two hours. Once the reaction was complete, the mixture was poured onto ice and made up to 250 ml by adding water. A transparent yellow solution was obtained which was used without further work-up in the azo coupling described below.

Synthesis of 2-{ethyl[4-(1,3-thiazol-2-yldiazenyl)phenyl]amino}ethyl sulfate, sodium salt will now be described. As to diazotization, 10.0 g (0.10 mol) of 2-aminothiazole were added to 300 ml of 60%, aqueous acetic acid solution. After adding 20 ml of concentrated sulfuric acid, the resultant mixture was cooled to 5° C. 40 ml of nitrosylsulfuric acid (40%) were then added dropwise, and the mixture was stirred for 2 hours with cooling to 0° C.

As to the azo coupling, the crude product of the coupling component, described above in connection with the synthesis of 2-[ethyl(phenyl)amino]ethyl hydrogensulfate, was added dropwise, with cooling to 10° C., to the previously freshly prepared diazonium salt solution. The batch was stirred overnight at room temperature. A pH value of 7 was then established by adding a 50% aqueous sodium hydroxide solution. On said addition, a red solid precipitated out, and was filtered out and dried. The solid was extracted by stirring with ethanol with heating and filtered in order to separate any inorganic salts still present. The filtrate was then completely evaporated. The yield was 31.4 g (88.2%).

Synthesis of 2-(ethyl{4-[(3-methyl-1,3-thiazol-3-ium-2-yl)diazenyl]phenyl}amino)ethyl sulfate (substantive dye 1) will now be described. 30.0 g (64.2 mmol) of 2-{ethyl[4-(1,3-thiazol-2-yldiazenyl)phenyl]amino}ethyl sulfate, sodium salt from the synthesis of 2-{ethyl[4-(1,3-thiazol-2-yldiazenyl)phenyl]amino}ethyl sulfate, sodium salt described above were stirred for 5 hours at 90° C. in 100 ml of p-toluenesulfonic acid methyl ester. The reaction solution changed to a deep dark blue color. After cooling, the batch was diluted with 100 ml of toluene. On dilution, a dark blue product precipitated out which was separated from the supernatant solution, washed with toluene, and then dried under a vacuum. The yield was 22.5 g (approx. 95%).

Synthesis Example 2

This Example regards the synthesis of 2-[{4-[(1,4-dimethyl-4H-1,2,4-triazol-1-ium-5-yl)diazenyl]phenyl}(ethyl)amino]ethyl sulfate (substantive dye 2), and includes the synthesis of 2-[ethyl(phenyl)amino]ethyl hydrogensulfate as described above in connection with Example 1.

Synthesis of 2-{ethyl[4-(1,2,4-thiazol-3-yldiazenyl)phenyl]amino}ethyl sulfate, sodium salt will now be described. As to diazotization, 8.4 g (0.10 mol) of 3-amino-1H-1,2,4-triazole were added to 300 ml of 60% acetic acid solution. After adding 20 ml of concentrated sulfuric acid, the resultant mixture was cooled to 5° C. 40 ml of nitrosylsulfuric acid (40%) were then added dropwise, and the mixture was stirred for 2 hours with cooling to 0° C.

As to the azo coupling, the crude product of the coupling component, described above in connection with the synthesis of 2-[ethyl(phenyl)amino]ethyl hydrogensulfate, was added dropwise, with cooling to 10° C., to the previously freshly prepared diazonium salt solution. The batch was stirred overnight at room temperature. A pH value of 7 was then established by adding a 50% aqueous sodium hydroxide solution. On said addition, an orange solid precipitated out which was filtered out and dried. The solid was extracted by stirring with ethanol with heating and filtered in order to separate any inorganic salts still present. The filtrate was then completely evaporated. The yield was 8.8 g (26.0%).

Synthesis of 2-[{4-[(1,4-dimethyl-4H-1,2,4-triazol-1-ium-5-yl)diazenyl]phenyl}(ethyl)amino]ethyl sulfate (substantive dye 2) will now be described. 7.6 g (22.3 mmol) of 2-{ethyl[4-(1,2,4-thiazol-3-yldiazenyl)phenyl]amino}ethyl sulfate, sodium salt from the synthesis of 2-{ethyl[4-(1,2,4- thiazol-3-yldiazenyl)phenyl]amino}ethyl sulfate, sodium salt described above were stirred for 5 hours at 90° C. in 50 ml of p-toluenesulfonic acid methyl ester. The reaction solution changed to a bright pink color. After cooling, the batch was diluted with 100 ml of toluene. On dilution, the product precipitated out in the form of a red solid which was filtered out, washed with toluene, and then dried under a vacuum. The product was soluble in water, producing a bright red color. The yield was 6.9 g (57%).

Synthesis Example 3

This synthesis example regards the synthesis of 2-(ethyl{4-[(3,6-methyl-1,3-benzothiazol-3-ium-2-yl)diazenyl]phenyl}amino)ethyl sulfate (substantive dye 3), and includes the synthesis of 2-[ethyl(phenyl)amino]ethyl hydrogensulfate as described above in connection with Example 1.

Synthesis of 2-{ethyl[4-(1,3-thiazol-2-yldiazenyl)phenyl]amino}ethyl sulfate, sodium salt will now be described. As to diazotization, 16.4 g (0.10 mol) of 2-amino-6-methylbenzothiazole were added to 300 ml of a 60% acetic acid solution. After adding 20 ml of concentrated sulfuric acid, the resultant mixture was cooled to 5° C. 40 ml of nitrosylsulfuric acid (40%) were then added dropwise, and the mixture was stirred for 2 hours with cooling to 0° C.

As to the azo coupling, the crude product of the coupling component, described above in connection with the synthesis of 2-[ethyl(phenyl)amino]ethyl hydrogensulfate, was added dropwise, with cooling to 10° C., to the previously freshly prepared diazonium salt solution. The batch was stirred overnight at room temperature. A pH value of 7 was then established by adding a 50% aqueous sodium hydroxide solution. On said addition, an violet solid precipitated out which was filtered out and dried. The solid was extracted by stirring with ethanol with heating and filtered in order to separate any inorganic salts still present. The filtrate was then completely evaporated. The product dissolved in water, producing a bright violet color. The yield was 28.5 g (62.5%).

Synthesis of 2-(ethyl{4-[(3,6-dimethyl-1,3-benzothiazol-3-ium-2-yl)diazenyl]phenyl}amino)ethyl sulfate (substantive dye 3) will now be described. 23.8 g (56.6 mmol) of 2-{ethyl[4-(6-methyl-1,3-benzothiazol-2-yldiazenyl)phenyl]amino}ethyl sulfate, sodium salt from step 1.3.2 were stirred for 5 hours at 90° C. in 100 ml of p-toluenesulfonic acid methyl ester. The reaction solution changed to a dark blue color. After cooling, the batch was diluted with 100 ml of toluene. On dilution, the product precipitated out in the form of a dark blue, pasty substance which was separated from the supernatant solvent phase, repeatedly extracted by stirring with toluene and then dried under a vacuum. The yield was 21.3 g (62.1%).

2. Coloration Examples

As to the production of coloring creams, the following coloring creams were produced:

TABLE 1

Example 1:
Nonionic Coloring Cream 1

| | |
|---|---|
| Cetearyl Alcohol | 6.0 g |
| Coconut Alcohol | 6.0 g |
| PEG-40 Hydrogenated Castor Oil | 1.0 g |
| Ceteareth-12 | 3.0 g |
| Ceteareth-20 | 3.0 g |
| PHB methyl ester | 0.3 g |
| PHB propyl ester | 0.2 g |

TABLE 1-continued

Example 1:
Nonionic Coloring Cream 1

| | |
|---|---|
| Phenoxyethanol | 1.0 g |
| PEG-8 | 5.0 g |
| Substantive dye according to the invention | 1.0 g |
| Ammonium sulfate | 1.0 g (in 30.0 g of water) |
| Hydroxyethylcellulose | 1.0 g (in 15.0 g of water) |
| NaOH 0.1% | ad pH value |
| Water | ad 100 |

The first nine components of Table 1 were melted together at 80° C., after which the dye was added. This mixture was emulsified with a solution of the substantive dye and of the ammonium sulfate in 30 g of water. A swelled preparation of 1.0 g of Natrosol 250 HR in 15.0 g of water was then added. The pH value stated in the table was established with 0.1% sodium hydroxide solution and then the mixture was made up to 100 g with water.

TABLE 2

Example 2:
Cationic Coloring Cream 2

| | |
|---|---|
| Cetearyl Alcohol | 4.0 g |
| Ceteareth-12 | 1.0 g |
| DEHYQUART A-CA | 2.0 g |
| Ammonium sulfate | 1.0 g (in 30.0 g of water) |
| Substantive dye according to the invention | 1.0 g |
| Water | ad 100 |

The Stenol 16/18 was melted together with Eumulgin B1 and Dehyquart A-CA, after which the melt was emulsified with hot water. The dye and the aqueous ammonium sulfate solution were then added. The pH value was adjusted to the value stated in the table with ammonia or citric acid and then the mixture was made up to 100 g with water.

TABLE 2

Example 3:
Anionic Coloring Cream 3

| | |
|---|---|
| Cetearyl Alcohol | 1.0 g |
| Coconut Alcohol | 1.0 g |
| AKYPO SOFT RLM 45N | 1.1 g |
| PHB propyl ester | 0.1 g |
| PHB methyl ester | 0.1 g |
| Ammonium sulfate | 1.0 g (in 30.0 g of water) |
| Substantive dye according to the invention | 1.0 g |
| Water | ad 100 |

The first five components of Table 3 were melted together. This melt was emulsified with hot water, the dye predissolved or predispersed in water was added thereto, and the ammonium sulfate solution was added. The pH value stated in the table was established with ammonia or citric acid and then the mixture was made up to 100 g with water.

List of raw materials used:
AKYPO RLM 45 NV laureth-5 carboxylate1 developed and distributed by Kao Corporation: auryl alcohol-4,5-EO-acetic acid sodium salt (min. active substance content 22);

DEHYQUART A-CA aqua (Water), cetrimonium chloride developed and distributed by BASF Societas Europaea: Trimethylhexadecylammonium chloride (approx. 24 26% active substance);

As to application of the coloring, 1.8 g portions of the coloring cream were applied onto approximately 6 cm long strands of human hair (Kerling natural European hair, blond), and left there for 30 minutes at 30° C. On completion of the period of exposure, the hair was rinsed, washed with a conventional shampoo, and dried. The strands of hair were colored in the shades stated below"

Substantive dye 1: 2-(ethyl{4-[(3-methyl-1,3-thiazol-3-ium-2-yl)diazenyl]phenyl}amino)ethyl sulfate Substantive dye 2: 2-[{4-[(1,4-dimethyl-4H-1,2,4-triazol-1-ium-5-yl)diazenyl]phenyl}(ethyl)amino]ethyl sulfate Substantive dye 3: 2-(ethyl{4-[(3,6-dimethyl-1,3-benzothiazol-3-ium-2-yl)diazenyl]phenyl}amino)ethyl sulfate

TABLE 3

Intensity of Coloring Applications

| Dye | Coloring cream | pH value | Color shade (intensity) |
|---|---|---|---|
| Substantive dye 1 | 1 | 7.0 | gentian blue (+++) |
| Substantive dye 1 | 1 | 9.5 | blue-black (+++) |
| Substantive dye 1 | 2 | 7.0 | dark blue (+++) |
| Substantive dye 1 | 2 | 9.5 | blue-black (+++) |
| Substantive dye 1 | 3 | 7.0 | gray-blue (++) |
| Substantive dye 1 | 3 | 9.5 | dark blue (+++) |
| Substantive dye 2 | 1 | 7.0 | purple (+++) |
| Substantive dye 2 | 1 | 9.5 | vivid red (+++) |
| Substantive dye 2 | 2 | 7.0 | red (++) |
| Substantive dye 2 | 2 | 9.5 | deep red (+++) |
| Substantive dye 2 | 3 | 7.0 | purple (+++) |
| Substantive dye 2 | 3 | 9.5 | vivid red (+++) |
| Substantive dye 3 | 1 | 7.0 | cobalt blue (++) |
| Substantive dye 3 | 1 | 9.5 | gray-blue (++) |
| Substantive dye 3 | 2 | 7.0 | deep blue (+++) |
| Substantive dye 3 | 2 | 9.5 | deep dark blue (+++) |
| Substantive dye 3 | 3 | 7.0 | ultramarine blue (+++) |
| Substantive dye 3 | 3 | 9.5 | deep dark blue (+++) |

Intensity:
+ = low
++ = medium
+++ = high

As demonstrated in Table 3, bright colorings with particularly high color intensity were obtained.

3. Verification of the Oxidation Stability of the Substantive Dyes (Ultrablonding Fastness)

Cream formulations were produced as depicted in Table 4 below from the listed components:

TABLE 4

| Cream Formulations | |
|---|---|
| Cetearyl Alcohol | 1.0 g |
| Coconut Alcohol | 1.0 g |
| AKYPO SOFT RLM 45N | 1.1 g |
| PHB propyl ester | 0.1 g |
| PHB methyl ester | 0.1 g |
| Ammonium sulfate | 1.0 g |
|  | (in 30.0 g of water) |
| Substantive dye according to the invention | 1.0 g |
| Water | ad 100 |

The first five components listed in Table 4 were melted together. This melt was emulsified with hot water, the dye predissolved or predispersed in water was added thereto, and the ammonium sulfate solution added. The pH value stated in the table was established with ammonia or citric acid and then the mixture was made up to 100 g with water.

The cream formulations were, in each case, mixed in a 1:1 ratio with a developer dispersion of the following composition depicted in Table 5:

TABLE 5

| Developer Dispersion | |
|---|---|
| Sodium hydroxide solution, 45% | 0.73 g |
| Dipicolinic acid | 0.10 g |
| Disodium pyrophosphate | 0.03 g |
| TURPINAL SL hydroxyethane-1,1-diphosphonic acid, 1-etidronic acid developed and distributed by Thermphos Dequest UK Ltd. | 1.50 g |
| TEXAPON NSO sodium laureth sulfate developed and distributed by BASF Societas Europaea | 2.00 g |
| Dow Corning DB 110 A (nonionic silicone emulsion) | 0.07 g |
| ACULYN 33A acrylates copolymer developed and distributed by Rohm & Haas Company | 15.00 g |
| Hydrogen peroxide, 50% | 22.40 g |
| Water | ad 100 |

As to a first example of the addition of persulfate, 100 g of the mixture obtained in mixing the developer dispersion into the cream formulations was then mixed with 8.33 g of potassium peroxydisulfate. The pH value of this finished mixture for use was between 9 and 10.2. For the blonding and coloring process, strands of hair (Kerling natural white) weighing approx. 0.7 g had 4 times the quantity of the finished mixture for use applied to them. Once the strands had been blonded for 30 minutes at 32° C., they were washed with a conventional commercial shampoo and dried with a hairdryer. The resultant colorings were then assessed visually under a daylight lamp.

TABLE 6

First Example of Intensity of Coloring Applications with the Addition of Persulfate

| Substantive dye | Color shade (intensity) |
|---|---|
| 2-(Ethyl{4-[(3-methyl-1,3-thiazol-3-ium-2-yl)diazenyl]phenyl}amino)ethyl sulfate (substantive dye 1) | mid-blue (+++) |
| 2-(Ethyl{4-[(3,6-dimethyl-1,3-benzothiazol-3-ium-2-yl)diazenyl]phenyl}amino) ethyl sulfate (substantive dye 3) | dark blue (+++) |
| Arianor Steel Blue (Basic Blue 99) comparison, conventional commercial blue dye | blond (-) |

Intensity:
(-) = no coloring any longer visible;
(+) = low;
(++) = medium;
(+++) = high As to a second example of the addition of persulfate, 100 g of the mixture obtained in mixing the developer dispersion into the cream formulations was mixed with 20 g of a mixture of ammonium peroxydisulfate, sodium peroxydisulfate, and potassium peroxydisulfate. The pH value of this finished mixture for use was between 9 and 10.2. For the blonding and coloring process, strands of hair (Kerling natural white) weighing approx. 0.7 g had 4 times the quantity of the finished mixture for use applied to them. Once the strands had been blonded for 30 minutes at 32° C., they were washed with a conventional commercial shampoo and dried with a hairdryer. The resultant colorings were then assessed visually under a daylight lamp.

TABLE 7

Second Example of Intensity of Coloring
Applications with the Addition of Persulfate

| Substantive dye | Color shade (intensity) |
|---|---|
| 2-(Ethyl{4-[(3-methyl-1,3-thiazol-3-ium-2-yl)diazenyl]phenyl}amino)ethyl sulfate (substantive dye 1) | gray-blue (+++) |
| 2-(Ethyl{4-[(3,6-dimethyl-1,3-benzothiazol-3-ium-2-yl)diazenyl]phenyl}amino) ethyl sulfate (substantive dye 3) | gray-blue (+++) |
| Arianor Steel Blue (Basic Blue 99) comparison, conventional commercial blue dye | blond (-) |

Intensity:
(-) = no coloring any longer visible;
(+) = low;
(++) = medium;
(+++) = high

What is claimed is:

1. An agent for coloring keratinic fibers included in a cosmetic carrier, the agent comprising:

at least one compound of the formula (I),

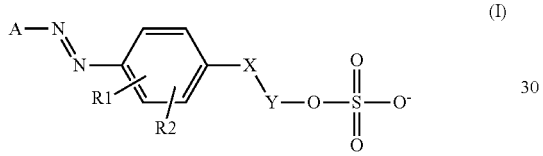

in which:

R1 and R2 mutually independently denote hydrogen, a $C_1$-$C_6$ alkyl group, a $C_2$-$C_6$ alkenyl group, a hydroxyl group, a $C_1$-$C_6$ alkoxy group, halogen, an amino group, an acetylamino group, a nitro group, or a nitrile group, or alternatively, R1 and R2 form a 5- or 6-membered, saturated or unsaturated, carbocyclic or heterocyclic ring if R1 and R2 are in ortho position relative to one another;

X denotes O or N—R3;

R3 denotes hydrogen, a $C_1$-$C_6$ alkyl group, a $C_2$-$C_6$ alkenyl group, a $C_2$-$C_6$ hydroxyalkyl group, a $C_2$-$C_6$ polyhydroxyalkyl group, a $C_1$-$C_6$ cyanoalkyl group, an aryl-$C_1$-$C_6$-alkyl group, or a group —Y'—O—SO$_2$—OM;

Y and Y', in each case, mutually independently denote $(CH_2)_n$, $C_2H_4$—$(OC_2H_4)_n$, $(CH_2)_n$—O—$(CH_2)_m$, or $(CH_2)_n$—N(R8)-$(CH_2)_m$, in which n and m in each case mutually independently denote an integer from 1 to 6, A denotes one of structures (II) to (XIII),

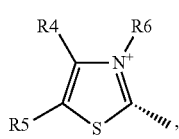

(II)

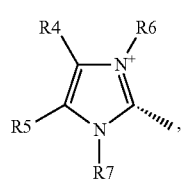

(III)

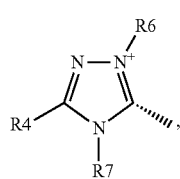

(IV)

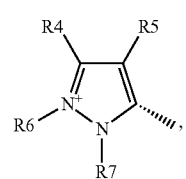

(V)

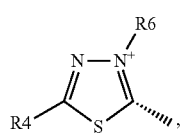

(VI)

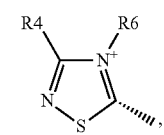

(VII)

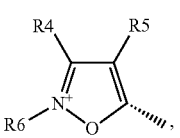

(VIII)

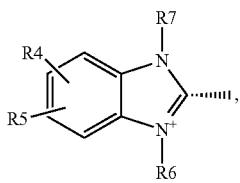 (IX)

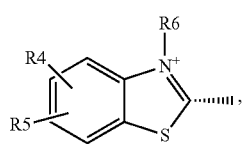 (X)

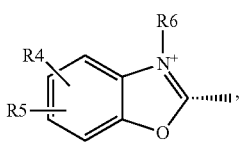 (XI)

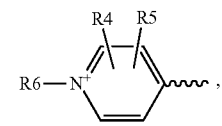 (XII)

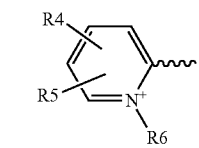 (XIII)

in which:
R4 and R5, in each case, mutually independently denote hydrogen, a $C_1$-$C_6$ alkyl group, a $C_2$-$C_6$ alkenyl group, a hydroxyl group, a $C_1$-$C_6$ alkoxy group, halogen, an amino group, an acetylamino group, a $C_1$-$C_6$ alkylsulfonyl group, or a nitrile group, or R4 and R5 form a 5- or 6-membered, saturated or unsaturated, carbocyclic or heterocyclic ring if R4 and R5 are in ortho position relative to one another;

R6 and R7 mutually independently denote a $C_1$-$C_6$ alkyl group, a $C_2$-$C_6$ alkenyl group, or a $C_2$-$C_6$ hydroxyalkyl group;

R8 denotes hydrogen, a $C_1$-$C_6$ alkyl group, a $C_2$-$C_6$ alkenyl group, or a $C_2$-$C_6$ hydroxyalkyl group; and M denotes hydrogen, an alkali metal or half an equivalent of an alkaline earth metal.

2. The agent of claim 1, wherein the agent comprises at least one compound of the formula (I), in which A denotes one of structures (II), (III), (IV), (VI), (VII), (IX), (X), (XII) or (XIII).

3. The agent of claim 1, further comprising at least one compound of the formula (I), in which X denotes N—R3 and Y denotes $(CH_2)_n$ with n equal to 2 or 3.

4. The agent of claim 1, further comprising at least one compound of the formula (I), in which X denotes N—R3 and R3 denotes a $C_1$-$C_6$ alkyl group, a $C_2$-$C_6$ alkenyl group, a methyl, or an ethyl group.

5. The agent of claim 1, further comprising at least one compound of the formula (I), in which R1 and R2 mutually independently denote hydrogen, a $C_1$-$C_6$ alkyl group, a $C_1$-$C_6$ alkoxy group, a halogen, or a hydrogen.

6. The agent of claim 1, further comprising at least one compound of the formula (I) selected from:
2-(methyl{4-[(3-methyl-1,3-thiazol-3-ium-2-yl)diazenyl]phenyl}amino)ethyl sulfate;
2-(ethyl{4-[(3-methyl-1,3-thiazol-3-ium-2-yl)diazenyl]phenyl}amino)ethyl sulfate;
3-(methyl{4-[(3-methyl-1,3-thiazol-3-ium-2-yl)diazenyl]phenyl}amino)propyl sulfate;
3-(ethyl{4-[(3-methyl-1,3-thiazol-3-ium-2-yl)diazenyl]phenyl}amino)propyl sulfate;
2-(methyl{3-methyl-4-[(3-methyl-1,3-thiazol-3-ium-2-yl)diazenyl]phenyl}amino)-ethyl sulfate;
3-(ethyl{3-methyl-4-[(3-methyl-1,3-thiazol-3-ium-2-yl)diazenyl]phenyl}amino)propyl sulfate;
2-[{4-[(1,3-dimethyl-1H-imidazol-3-ium-2-yl)diazenyl]phenyl}(methyl)amino]ethyl sulfate;
2-[{4-[(1,3-dimethyl-1H-imidazol-3-ium-2-yl)diazenyl]phenyl}(ethyl)amino]ethyl sulfate;
3-[{4-[(1,3-dimethyl-1H-imidazol-3-ium-2-yl)diazenyl]phenyl}(ethyl)amino]propyl sulfate;
2-[{4-[(1,3-dimethyl-1H-imidazol-3-ium-2-yl)diazenyl]-3-methylphenyl}(ethyl)amino]ethyl sulfate;
3-[{4-[(1,3-dimethyl-1H-imidazol-3-ium-2-yl)diazenyl]-3-methylphenyl}(ethyl)amino]propyl sulfate;
2-[{4-[(1,4-dimethyl-4H-1,2,4-triazol-1-ium-5-yl)diazenyl]phenyl}(methyl)amino]ethyl sulfate;
2-[{4-[(1,4-dimethyl-4H-1,2,4-triazol-1-ium-5-yl)diazenyl]phenyl}(ethyl)amino]ethyl sulfate;
3-[{4-[(1,4-dimethyl-4H-1,2,4-triazol-1-ium-5-yl)diazenyl]phenyl}(ethyl)amino]propyl sulfate;
3-[{4-[(1,4-dimethyl-4H-1,2,4-triazol-1-ium-5-yl)diazenyl]-3-methylphenyl}(methyl)amino]propyl sulfate;
3-[{4-[(1,4-dimethyl-4H-1,2,4-triazol-1-ium-5-yl)diazenyl]-3-methylphenyl}(ethyl)amino]propyl sulfate;
2-(methyl{4-[(3-methyl-1,3,4-thiadiazol-3-ium-2-yl)diazenyl]phenyl}amino)ethyl sulfate;
2-(ethyl{4-[(3-methyl-1,3,4-thiadiazol-3-ium-2-yl)diazenyl]phenyl}amino)ethyl sulfate;
3-(ethyl{4-[(3-methyl-1,3,4-thiadiazol-3-ium-2-yl)diazenyl]phenyl}amino)propyl sulfate;
3-(methyl{3-methyl-4-[(3-methyl-1,3,4-thiadiazol-3-ium-2-yl)diazenyl]phenyl}amino)propyl sulfate;
3-(ethyl{3-methyl-4-[(3-methyl-1,3,4-thiadiazol-3-ium-2-yl)diazenyl]phenyl}amino)propyl sulfate;
2-(methyl{4-[(4-methyl-1,2,4-thiadiazol-4-ium-5-yl)diazenyl]phenyl}amino)ethyl sulfate;
2-(ethyl{4-[(4-methyl-1,2,4-thiadiazol-4-ium-5-yl)diazenyl]phenyl}amino)ethyl sulfate;
3-(ethyl{4-[(4-methyl-1,2,4-thiadiazol-4-ium-5-yl)diazenyl]phenyl}amino)propyl sulfate;
2-(methyl{3-methyl-4-[(4-methyl-1,2,4-thiadiazol-4-ium-5-yl)diazenyl]phenyl}amino)ethyl sulfate;
3-(ethyl{3-methyl-4-[(4-methyl-1,2,4-thiadiazol-4-ium-5-yl)diazenyl]phenyl}amino)propyl sulfate;
2-(methyl{4-[(3-methyl-1,3-benzothiazol-3-ium-2-yl)diazenyl]phenyl}amino)ethyl sulfate;

2-(ethyl{4-[(3-methyl-1,3-benzothiazol-3-ium-2-yl)diazenyl]phenyl}amino)ethyl sulfate;
2-(ethyl{4-[(3,6-dimethyl-1,3-benzothiazol-3-ium-2-yl)diazenyl]phenyl}amino)ethyl sulfate;
3-(ethyl{4-[(3-methyl-1,3-benzothiazol-3-ium-2-yl)diazenyl]phenyl}amino)propyl sulfate;
2-(methyl{3-methyl-4-[(3-methyl-1,3-benzothiazol-3-ium-2-yl)diazenyl]phenyl}amino)ethyl sulfate;
3-(ethyl{3-methyl-4-[(3-methyl-1,3-benzothiazol-3-ium-2-yl)diazenyl]phenyl}amino)propyl sulfate;
2-[{4-[(1,3-dimethyl-1H-benzimidazol-3-ium-2-yl)diazenyl]phenyl}(methyl)amino]ethyl sulfate;
2-[{4-[(1,3-dimethyl-1H-benzimidazol-3-ium-2-yl)diazenyl]phenyl}(ethyl)amino]ethyl sulfate;
3-[{4-[(1,3-dimethyl-1H-benzimidazol-3-ium-2-yl)diazenyl]phenyl}(ethyl)amino]propyl sulfate;
2-[{4-[(1,3-dimethyl-1H-benzimidazol-3-ium-2-yl)diazenyl]-3-methylphenyl}(methyl)amino]ethyl sulfate; and
3-[{4-[(1,3-dimethyl-1H-benzimidazol-3-ium-2-yl)diazenyl]-3-methylphenyl}(ethyl)amino]propyl sulfate.

7. The agent of claim 1, further comprising the compounds of the formula (I), in each case, in a quantity of 0.001 to 5 wt. % relative to the total weight of the agent.

8. The agent of claim 1, further comprising at least one oxidizing agent selected from hydrogen peroxide, a solid addition product thereof onto organic or inorganic compounds, sodium persulfate, potassium persulfate or ammonium persulfate.

9. The agent of claim 1, further comprising 0.5 to 15 wt. % of hydrogen peroxide, in each case, relative to the total weight of the agent.

10. The agent of claim 1, further comprising persulfates in a quantity of 1.5 to 60 wt. % relative to the total weight of the agent.

11. The agent of claim 1, further comprising at least one complexing agent from the group of nitrogen—including polycarboxylic acids, Ethylenediaminetetraacidic acid (EDTA), Ethylenediamine-N,N'-disuccinic acid (EDDS), phosphonates, 1-hydroxyethane-1,1-diphosphonate (HEDP), ethylenediaminetetramethylenephosphonate (EDTMP), diethylenetriaminepentamethylenephosphonate (DTPMP), sodium salts thereof, or combinations thereof.

12. The agent of claim 1, further comprising at least one anionic surfactant.

13. The agent of claim 1, further comprising at least one amphoteric surfactant.

14. The agent of claim 1, wherein the agent is applied to keratinic fibers.

15. Compounds of the formula (I),

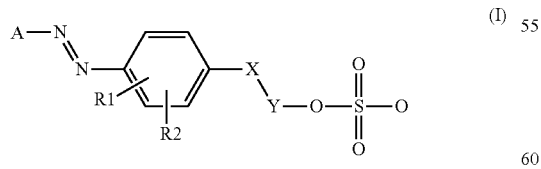

in which:
R1 and R2 mutually independently denote hydrogen, a $C_1$-$C_6$ alkyl group, a $C_2$-$C_6$ alkenyl group, a hydroxyl group, a $C_1$-$C_6$ alkoxy group, halogen, an amino group, an acetylamino group, a nitro group, or a nitrile group, or alternatively, R1 and R2 form a 5- or 6-membered, saturated or unsaturated, carbocyclic or heterocyclic ring if R1 and R2 are in ortho position relative to one another;

X denotes O or N—R3;

R3 denotes hydrogen, a $C_1$-$C_6$ alkyl group, a $C_2$-$C_6$ alkenyl group, a $C_2$-$C_6$ hydroxyalkyl group, a $C_2$-$C_6$ polyhydroxyalkyl group, a $C_1$-$C_6$ cyanoalkyl group, an aryl-$C_1$-$C_6$-alkyl group, or a group —Y'—O—SO$_2$—OM;

Y and Y', in each case, mutually independently denote $(CH_2)_n$, $C_2H_4$—$(OC_2H_4)_n$, $(CH_2)_n$—O—$(CH_2)_m$, or $(CH_2)_n$—N(R8)-$(CH_2)_m$, in which n and m, in each case, mutually independently denote an integer from 1 to 6;

A denotes one of structures (II) to (XIII),

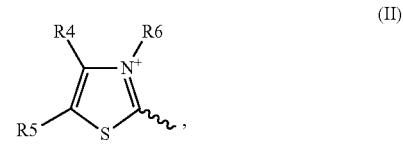

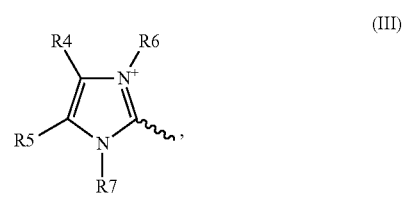

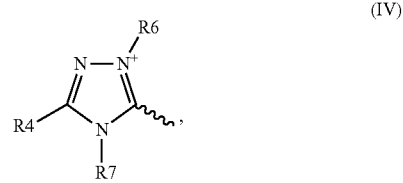

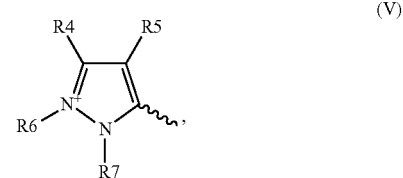

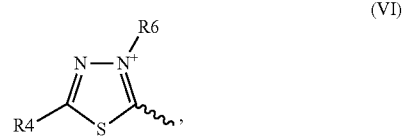

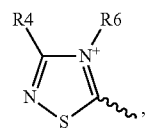 (VI)

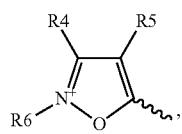 (VIII)

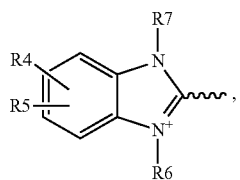 (IX)

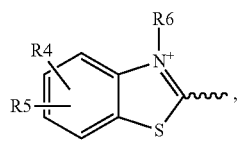 (X)

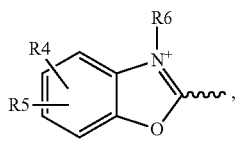 (XI)

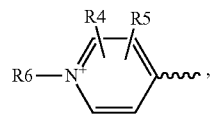 (XII)

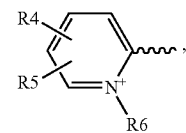 (XIII)

in which:
R4 and R5, in each case, mutually independently denote hydrogen, a $C_1$-$C_6$ alkyl group, a $C_2$-$C_6$ alkenyl group, a hydroxyl group, a $C_1$-$C_6$ alkoxy group, halogen, an amino group, an acetylamino group, a $C_1$-$C_6$ alkylsulfonyl group, or a nitrile group, or R4 and R5 form a 5- or 6-membered, saturated or unsaturated, carbocyclic or heterocyclic ring if R4 and R5 are in ortho position relative to one another;

R6 and R7 mutually independently denote a $C_1$-$C_6$ alkyl group, a $C_2$-$C_6$ alkenyl group, or a $C_2$-$C_6$ hydroxyalkyl group;

R8 denotes hydrogen, a $C_1$-$C_6$ alkyl group, a $C_2$-$C_6$ alkenyl group, or a $C_2$-$C_6$ hydroxyalkyl group, and M denotes hydrogen, an alkali metal or half an equivalent of an alkaline earth metal.

\* \* \* \* \*